(12) United States Patent
Gibson et al.

(10) Patent No.: US 11,826,949 B2
(45) Date of Patent: Nov. 28, 2023

(54) PARTICLE STEREOLITHOGRAPHY

(71) Applicant: Desktop Metal, Inc., Burlington, MA (US)

(72) Inventors: Michael Andrew Gibson, Boston, MA (US); Jonah Samuel Myerberg, Lexington, MA (US); Ricardo Fulop, Lexington, MA (US); Michael J. Tarkanian, West Roxbury, MA (US); Yet-Ming Chiang, Weston, MA (US); Jay Tobia, Cambridge, MA (US); Olivia Molnar Lam, Burlington, MA (US)

(73) Assignee: Desktop Metal, Inc., Burlington, MA (US)

( * ) Notice: Subject to any disclaimer, the term of this patent is extended or adjusted under 35 U.S.C. 154(b) by 1006 days.

(21) Appl. No.: 16/328,448

(22) PCT Filed: Nov. 14, 2017

(86) PCT No.: PCT/US2017/061580
§ 371 (c)(1),
(2) Date: Feb. 26, 2019

(87) PCT Pub. No.: WO2018/090019
PCT Pub. Date: May 17, 2018

(65) Prior Publication Data
US 2021/0237347 A1    Aug. 5, 2021

Related U.S. Application Data

(63) Continuation-in-part of application No. 62/474,014, filed on Mar. 20, 2017, and a continuation-in-part of application No. 62/421,716, filed on Nov. 14, 2016.

(51) Int. Cl.
*B29C 64/124* (2017.01)
*B29C 64/245* (2017.01)
(Continued)

(52) U.S. Cl.
CPC ............ *B29C 64/124* (2017.08); *A61K 6/807* (2020.01); *A61K 6/818* (2020.01); *A61K 6/822* (2020.01);
(Continued)

(58) Field of Classification Search
CPC ......... A61L 27/46; A61K 6/807; A61K 6/818; A61K 6/822; A61K 6/833; B22F 1/10;
(Continued)

(56) References Cited

U.S. PATENT DOCUMENTS 7,461,684 B2 * 12/2008 Liu ........................... B22C 9/04
164/97
2005/0161189 A1 * 7/2005 Sercombe .............. B33Y 10/00
164/97

(Continued)

*Primary Examiner* — Michael M. Robinson
(74) *Attorney, Agent, or Firm* — Hansen IP Law PLLC

(57) ABSTRACT

Systems, methods, components, and materials are disclosed for stereolithographic fabrication of three-dimensional, dense objects. A resin including at least one component of a binder system and dispersed particles can be exposed to an activation light source. The activation light source can cure the at least one component of the binder system to form a green object, which can include the at least one component of the binder system and the particles. A dense object can be formed from the green object by removing the at least one component of the binder system in an extraction process and thermally processing particles to coalesce into the dense object.

11 Claims, 18 Drawing Sheets

(51) Int. Cl.

| | |
|---|---|
| B29C 64/165 | (2017.01) |
| B33Y 70/10 | (2020.01) |
| C04B 35/486 | (2006.01) |
| C04B 35/626 | (2006.01) |
| C04B 35/632 | (2006.01) |
| C04B 35/638 | (2006.01) |
| G03F 7/00 | (2006.01) |
| G03F 7/004 | (2006.01) |
| A61K 6/807 | (2020.01) |
| A61K 6/818 | (2020.01) |
| A61K 6/822 | (2020.01) |
| A61K 6/833 | (2020.01) |
| C04B 35/01 | (2006.01) |
| C04B 35/634 | (2006.01) |
| B22F 1/10 | (2022.01) |
| B22F 10/12 | (2021.01) |
| B22F 10/50 | (2021.01) |
| A61L 27/46 | (2006.01) |
| B33Y 50/02 | (2015.01) |
| B29C 64/135 | (2017.01) |
| B22F 7/04 | (2006.01) |
| B28B 1/00 | (2006.01) |
| B33Y 10/00 | (2015.01) |
| B22F 3/26 | (2006.01) |
| B22F 7/08 | (2006.01) |
| B33Y 80/00 | (2015.01) |
| B82Y 30/00 | (2011.01) |
| B82Y 40/00 | (2011.01) |
| C22C 9/06 | (2006.01) |
| C22C 19/03 | (2006.01) |
| B22F 12/90 | (2021.01) |
| B22F 10/64 | (2021.01) |
| B22F 1/102 | (2022.01) |
| G03F 7/027 | (2006.01) |
| B22F 3/10 | (2006.01) |
| B29K 509/02 | (2006.01) |

(52) U.S. Cl.
CPC ............. *A61K 6/833* (2020.01); *A61L 27/46* (2013.01); *B22F 1/10* (2022.01); *B22F 3/26* (2013.01); *B22F 7/04* (2013.01); *B22F 7/08* (2013.01); *B22F 10/12* (2021.01); *B22F 10/50* (2021.01); *B28B 1/001* (2013.01); *B29C 64/135* (2017.08); *B29C 64/165* (2017.08); *B29C 64/245* (2017.08); *B33Y 10/00* (2014.12); *B33Y 50/02* (2014.12); *B33Y 70/10* (2020.01); *C04B 35/013* (2013.01); *C04B 35/486* (2013.01); *C04B 35/6263* (2013.01); *C04B 35/6264* (2013.01); *C04B 35/632* (2013.01); *C04B 35/634* (2013.01); *C04B 35/638* (2013.01); *C04B 35/63488* (2013.01); *G03F 7/0037* (2013.01); *G03F 7/0047* (2013.01); *G03F 7/70416* (2013.01); *B22F 1/102* (2022.01); *B22F 3/1021* (2013.01); *B22F 10/64* (2021.01); *B22F 12/90* (2021.01); *B22F 2007/042* (2013.01); *B22F 2998/10* (2013.01); *B29K 2509/02* (2013.01); *B33Y 80/00* (2014.12); *B82Y 30/00* (2013.01); *B82Y 40/00* (2013.01); *C22C 9/06* (2013.01); *C22C 19/03* (2013.01); *G03F 7/027* (2013.01)

(58) Field of Classification Search
CPC ...... B22F 1/17; B22F 3/26; B22F 7/04; B22F 7/08; B22F 10/10; B22F 10/20; B22F 1/16; B22F 3/1021; B22F 2007/042; B22F 2998/10; B28B 1/001; B29C 64/135; B29C 64/165; B29C 64/245; B29C 64/129; B29C 64/124; B33Y 10/00; B33Y 50/02; B33Y 70/00; B33Y 70/10; B33Y 80/00; C04B 35/013; C04B 35/486; C04B 35/6263; C04B 35/6264; C04B 35/632; C04B 35/634; C04B 35/63488; C04B 35/638; G03F 7/0037; G03F 7/0047; G03F 7/70416; G03F 7/027; B29K 2509/02; B82Y 30/00; B82Y 40/00; C22C 9/06; C22C 19/03; Y02P 10/25

See application file for complete search history.

(56) References Cited

U.S. PATENT DOCUMENTS

| | | | | |
|---|---|---|---|---|
| 2007/0072762 A1* | 3/2007 | Neil | .......................... | B28B 1/00 264/401 |
| 2011/0260365 A1* | 10/2011 | El-Siblani | .............. | B33Y 80/00 264/401 |
| 2017/0129175 A1* | 5/2017 | Zitelli | ............... | G02F 1/133514 |
| 2018/0318922 A1* | 11/2018 | Valls Anglés | ......... | C22C 1/0416 |

* cited by examiner

PARTICLE STEREOLITHOGRAPHY

CROSS-REFERENCE TO RELATED APPLICATIONS

This application claims priority to U.S. Prov. App. No. 62/421,716, filed Nov. 14, 2016, and to U.S. Prov. App. No. 62/474,014, filed Mar. 20, 2017, with the entire contents of each of these applications hereby incorporated herein by reference.

BACKGROUND

Stereolithography is an additive manufacturing technique for fabricating a three-dimensional object. Systems using this technique control the incidence of a light source on a liquid polymer to cause controlled, local hardening of the polymer and, ultimately, to build the three-dimensional object layer-by-layer. The result is a three-dimensional object made of one or more polymers and, thus, subject to the physical limitations of those constituent polymers.

SUMMARY

Systems, methods, components, and materials are disclosed for stereolithographic fabrication of three-dimensional, dense objects. A resin including at least one component of a binder system and dispersed particles can be exposed to an activation light source. The activation light source can cure the at least one component of the binder system to form a green object, which can include the at least one component of the binder system and the metal particles. A dense object can be formed from the green object by removing the at least one component of the binder system in an extraction process and thermally processing the particles to coalesce into the dense object.

According to one aspect, a resin can include a first binder, a second binder different from the first binder and in a mixture with the first binder, and particles (e.g., metal, ceramic, or a combination thereof) suspended in the mixture of the first binder and the second binder. The particles can be thermally processable to coalesce with one another into a mass, at least one of the first binder and the second binder can be reactive to crosslink or polymerize upon sufficient exposure of the first binder and the second binder to a predetermined wavelength of light, and the first binder and the second binder can be separately extractable from the mass following crosslinking or polymerization of the at least one of the first binder and the second binder.

In some implementations, the particles can be sinterable to coalesce with one another into the mass. Further or instead, the particles can be infiltratable with a liquid metal to coalesce with one another into the mass.

In certain implementations, the first binder can be substantially non-reactive under exposure to the predetermined wavelength of light sufficient to cross-link or polymerize the second binder.

In some implementations, the first binder can include a wax extractable from the second binder by chemical solvation in a non-polar chemical following sufficient exposure of the first binder and the second binder to the predetermined wavelength of light to crosslink or polymerize the second binder.

In certain implementations, the first binder can include a plurality of low-molecular weight constituents, each constituent extractable from the second binder by a chemical solution following sufficient exposure of the first binder and the second binder to the predetermined wavelength of light sufficient to crosslink or polymerize the second binder.

In some implementations, the resin can be a non-Newtonian fluid at 25° C.

In certain implementations, exposure to light at a wavelength of about 300 nm to about 450 nm is sufficient to crosslink or polymerize at least one of the first binder and the second binder.

In some implementations, the resin can further include one or more of a photo-absorber or a photo-initiator suspended in the mixture including the first binder and the second binder.

In certain implementations, a concentration by volume of the particles in the resin is within ±25 percent of a tap density of the particles.

In some implementations, the first binder can include one or more of the following: paraffin wax, carnauba wax, stearic acid, polyethylene glycol, polyoxymethylene, oleic acid, and dibutyl phthalate. Further or instead, the second binder can include one or more of the following: poly(methyl methacrylate), polyethylene glycol diacrylate, urethane oligomers functionalized to acrylate groups, epoxy oligomers functionalized to acrylate groups, 1,6-Hexanediol acrylates, or styrene.

According to another aspect a method of additive manufacturing of a three-dimensional object can include providing a layer of a resin on a media source, the resin including particles suspended in a mixture of a first binder and a second binder, directing light energy onto each layer of a plurality of layers of the resin to crosslink or polymerize at least one of the first binder and the second binder of the resin on a substrate carried by a build plate, the light energy directed onto the resin in a respective predetermined pattern associated with each layer to form a three-dimensional object, thermally processing the particles in the three-dimensional object to coalesce the particles to one another, extracting the first binder from the three-dimensional object in a primary debinding process, and extracting the second binder from the three-dimensional object in a secondary debinding process different from the primary debinding process.

In certain implementations, thermally processing the particles in the three-dimensional object can include sintering the three-dimensional object. Additionally, or alternatively, thermally processing the particles in the three-dimensional object can include infiltrating the three-dimensional object with a liquid metal. Further, or instead, thermally processing the particles in the three-dimensional object can include thermally-activating pyrolysis of at least one of the first binder and the second binder into a ceramic.

In some implementations, one or both of the primary debinding process and the secondary debinding process can include thermal debinding, chemical debinding, or a combination thereof.

In certain implementations, directing light energy onto each layer of the plurality of layers of the resin can include crosslinking or polymerizing the first binder and the second binder, and the primary debinding process includes breaking down the crosslinked or polymerized first binder. For example, the first binder can include acrylic anhydride, methacrylic anhydride, or a combination thereof.

According to another aspect, a method of additive manufacturing can include providing a layer of a resin on a media source disposed within a working volume defined by a build chamber, curing discrete portions of the layer of the resin on a substrate carried on a surface of a build plate in the working volume, separating the cured discrete portions of the layer from the media source, wherein the separation of at least one of the cured discrete portions is independent of the separation of at least another one of the cured discrete portions, and, for a plurality of layers, repeating the steps of providing each respective layer of the resin, curing discrete portions of each respective layer of the resin, and separating the cured discrete portions of each respective layer of the resin to form a three-dimensional object.

In certain implementations, the resin can include particles suspended in at least one binder, and curing discrete portions of each respective layer of the resin can include crosslinking or polymerizing the at least one binder.

In some implementations, curing the discrete portions of each respective layer can include, along each discrete portion of the respective layer of the resin, directing light energy into the working volume through a transparent portion of the media source, the light energy sufficient to cure at least one component of the resin. For example, separating the cured discrete portions of each respective layer of the resin from the media source can include moving one or both of the build plate and the transparent portion of the media source relative to one another. As another or additional example, separating the cured discrete portions of each respective layer of the resin from the media source can include substantially continuously moving of one or both of the build plate and the transparent portion of the media source relative to one another. Further or instead, curing the discrete portions of each respective layer of the resin can include substantially continuously curing adjacent discrete portions of the respective layer of the resin.

In certain implementations, separating the cured discrete portions of each respective layer of the resin from the media source can include moving one or both of the build plate and the transparent portion of the media source in a direction having a component parallel to the layer of the resin. Further or instead, each discrete segment of each respective layer of the resin spans a dimension of the surface of the build plate. Continuing with this example, separating the cured discrete portions of each respective layer of the resin from the media source can include moving the transparent portion of the media source in a direction transverse to the spanned dimension of the surface build plate.

In some implementations, at least one cured discrete portion of each respective layer of the resin can be separated from the media source before curing at least another discrete portion of the respective layer. For example, at least one cured discrete portion of each respective layer of the resin can be separated from the media before curing an adjacent discrete portion of the respective layer of the resin.

According to still another aspect, a stereolithography system can include a build chamber defining a working volume, a build plate disposed within the working volume, the build plate having a surface, an activation light source, and a media source disposed within the working volume, the media source including a transparent portion, the activation light source positioned to direct activation light, through the transparent portion of the media source, to the surface of the build plate, and one or both of the build plate and the transparent portion of the media source movable relative to one another to change a position of the transparent portion of the media source by an increment substantially equal to a width of the transparent portion of the media source in a direction parallel to the surface of the build plate.

In certain implementations, the width of the transparent portion of the media source can be less than a dimension of the surface of the build plate in a direction of the changed position of the transparent portion of the media source.

In some implementations, the transparent portion of the media source can be movable relative to the build plate along the direction parallel to the surface of the build plate.

In certain implementations, the build plate can be movable relative to the transparent portion of the media source along the direction parallel to the surface of the build plate.

In certain implementations, the media source can further include a dispersion section, a collection section, and a reservoir in fluid communication with the dispersion section and the collection section, the dispersion section along a first side of the transparent portion of the media source, the collection section along a second side, different from the first side, of the transparent portion of the media source, and the dispersion section and the collection section. The media source can further include a blade movable to spread resin from the dispersion section across the transparent portion of the media source.

In some implementations, the transparent portion of the media source can span a dimension of the surface of the build plate. At least one of the build plate and the transparent portion of the media source can be movable, for example, in a direction transverse to the spanned dimension of the surface of the build plate.

In certain implementations, the activation light source can be a light source having a wavelength of about 300 nm to about 350 nm.

According to yet another aspect, a resin can include particles of a first material, particles of a second material, the second material different from the first material, and a binder system in which the particles of the first material and the particles of the second material are suspended, the particles of the first material substantially transparent to light of a wavelength sufficient to crosslink, polymerize, or both, at least one component of the binder system.

In certain implementations, the particles of the first material and the particles of the second material can be substantially homogeneously suspended in the binder system.

In some implementations, the particles of the second material can be substantially opaque to light of the wavelength sufficient to crosslink, polymerize, or both, the at least one component of the binder system.

In certain implementations, the particles of the second material can have an average size less than the wavelength of the light sufficient to crosslink, polymerize, or both, the at least one component of the binder system.

In some implementations, the particles of the first material can include a ceramic. Further or instead, the particles of the second material can include a metal.

In certain implementations, the first material can be chemically convertible to the second material. For example, the first material can be chemically convertible to the second material via thermally-activated decomposition or reduction.

In some implementations, the first material can be a metal oxide reduceable to form a metal.

In certain implementations, first material can include a ceramic, an intermetallic, or both, and the particles of the first material are chemically convertible to a first metal, and the particles of a second material include a second metal alloyable with the first metal. The particles of the first material can be in a relative concentration to the particles of the second material such that an alloy of the first metal and the second metal meets a predetermined material standard. Further or instead, an oxide of the first metal can be less chemically stable than an oxide of the second metal.

In some implementations, the binder system can include a first binder and a second binder, the first binder different from the second binder and in a mixture with the first binder, and the first binder substantially non-reactive under exposure to the wavelength of light sufficient to crosslink or polymerize the second binder.

In certain implementations, the first binder can be extractable from the second binder following exposure of the second binder to the wavelength of light sufficient to crosslink or polymerize the second binder.

According to yet another aspect, a method of additive manufacturing of the three-dimensional object can include providing a layer of a resin on a media source, the resin including particles of a first material, particles of a second material, the second material different from the first material, and a binder system in which the particles of the first material and the particles of the second material are suspended, directing light energy in a predetermined pattern onto the layer to cure the resin on a substrate carried by a build plate, the particles of the first material substantially transparent to the light energy, and the light energy crosslinking, polymerizing, or both, at least one component of the binder system, and for each layer of a plurality of layers, repeating the steps of providing each respective layer of the resin, and directing light energy in a predetermined pattern onto each respective layer of the resin to form a three-dimensional object.

In certain implementations, the light energy directed onto each layer can penetrate the respective layer to bond successive layers of the plurality of layers of the three-dimensional object.

In some implementations, the method can further include sintering the three-dimensional object, the sintering transforming the particles of the first material to a metal or an additive in a metallic alloy.

In certain implementations, the method can further include removing the binder system from the three-dimensional object through a plurality of debinding processes.

In some implementations, the method can further include infiltrating the three-dimensional object with a liquid metal. For example, infiltrating the three-dimensional object with the liquid metal can include replacing the binder system with the liquid metal.

Other aspects, features, and advantages will be apparent from the description and drawings, and from the claims.

BRIEF DESCRIPTION OF THE DRAWINGS

Like reference symbols in the various drawings indicate like elements.

DESCRIPTION

Figure 1:
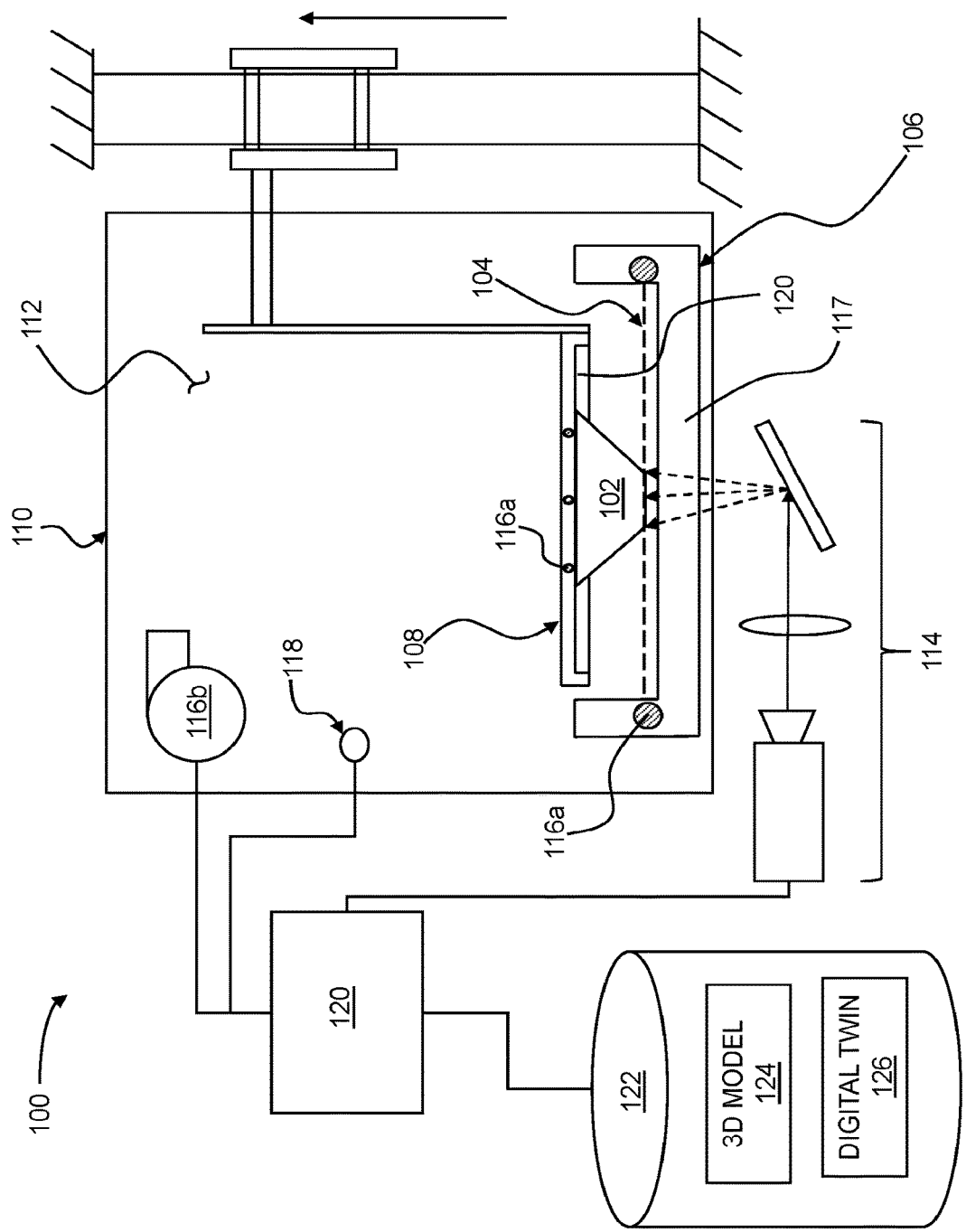
FIG. 1 is a schematic representation of a stereolithography system.

Embodiments will now be described with reference to the accompanying figures. The foregoing may, however, be embodied in many different forms and should not be construed as limited to the implementations set forth herein.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" and the term "and" should each generally be understood to mean "and/or.".

As used herein, the term "substrate" should be generally understood to be a surface upon which a layer is formed. Accordingly, the term substrate should be understood to include a surface of a build plate, a coating on a surface of a build plate, a previously formed layer of a three-dimensional object being formed, and combinations thereof, unless otherwise specified or made clear from the context.

As used herein, the term "binder system" should be generally understood to include a plurality of binders, and is used interchangeably with the recitation of the plurality of binders. Thus, for example, a first binder and a second binder in a resin should be understood to be a binder system of the resin, unless otherwise specified or made clear from the context.

As used herein, the term "mixture" should be generally understood to include an aggregate of two or more substances that are not chemically united and, thus, should be understood to include a solution of two or more substances.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," or the like) provided herein, is intended merely to better describe the embodiments and does not pose a limitation on the scope of the embodiments. No language in the specification should be construed as indicating any unclaimed element as essential to the practice of the embodiments.

In the following description, it is understood that terms such as "first," "second," "top," "bottom," "up," "down," and the like, are words of convenience and are not to be construed as limiting terms. Thus, particularly, recitation of first and second should not be construed to imply any particular order.

Referring now to FIG. 1A, a stereolithography system 100 can be used to form a three-dimensional object 102 from a resin 104 by selectively exposing the resin 104 to activation energy from an activation light source 114. The resin 104 can include particles (e.g., metal, ceramic, or a combination thereof) suspended in a plurality of binders, which can include a first binder and a second binder. While the resin 104 can include the first binder and the second binder, it should be appreciated that the resin 104 can include a greater number of binders without departing from the scope of the present disclosure.

In general, the second binder can be different from the first binder and in a mixture with the first binder to form the resin 104 with characteristics particularly suitable for stereolithographic fabrication of dense objects. For example, as described in greater detail below, at least one of the first binder and the second binder can have an increased resistance to deformation upon exposure to light having a predetermined wavelength, and the first binder and the second binder can be separately extractable from the three-dimensional object 102. Thus, for example, the first binder and the second binder, in combination, can address the challenges of handling the resin 104 in the stereolithography system 100 while having mechanical and/or chemical properties useful for forming the three-dimensional object 102. Through layer-by-layer exposure of the resin 104 to activation light, a green part, such as the three-dimensional object 102, can be formed. As also described in greater detail below, the first binder and the second binder can be extracted (e.g., separately extracted) from the three-dimensional object 102, and the three-dimensional object 102 can be densified to form a finished part. As compared to a part formed only from polymeric materials, it should be appreciated that the resulting finished part formed through densification of the particles of the resin 104 can have improved strength, particularly in instances in which the particles include metal and/or ceramic material.

The stereolithography system 100 can be an inverted system including a media source 106 and a build plate 108. The inverted orientation of the stereolithography system 100 can facilitate, among other things, draining excess amounts of the resin 104 from the three-dimensional object 102 and back toward the media source 106 under the force of gravity. In use, the media source 106 can carry the resin 104, and the build plate 108 can move in a direction away from the media source 108 as the three-dimensional object 102 is built through layer-by-layer exposure of the second binder in the resin 104 on the media source 106 to activation light. More specifically, the stereolithography system 100 can include a build chamber 110 defining a working volume 112, in which the media source 106 and the build plate 108 can be disposed, and the stereolithography system 100 can include an activation light source 114 positioned to direct activation light, as described in greater detail below, into the working volume 112 in a direction toward the media source 106 and the build plate 108. Continuing with this example, light from the activation light source 114 can be controlled to be incident on the resin 104 carried by the media source 106 to modify the second binder in the resin 104 in a predetermined pattern to form a layer of the three-dimensional object 102 on a substrate (e.g., the build plate 108 or a previous layer of the three-dimensional object 102).

The stereolithography system 100 can include a heater 116a,b in thermal communication with the media source 106 and controllable to heat the media source 106 to a first target temperature (e.g., greater than about 50° C.), thus heating the resin 104 carried by the media source 106. The first target temperature can be, for example, greater than a melt temperature of the first binder of the resin 104. Thus, heating the media source 106 can facilitate spreading the resin 104 on the media source 106 prior to activating the second binder of the resin 104 and, further or instead, can facilitate removal of the first binder following activation of the second binder of the resin 104.

The heater 116a,b can be any type and number of heaters sufficient to create a desired thermal profile within the working volume 112. Accordingly, the heater 116a,b can be spatially distributed in the working volume 112. Additionally, or alternatively, the heater 116a,b can transfer heat within the working volume 112 through conduction, forced convection, natural convection, radiation, or combinations thereof. As used herein, conduction includes heat transfer through a medium that is solid, semi-solid, liquid, or combinations thereof. Thus, for example, heat transfer from the media source 106 to the resin 104 should be understood to occur primarily through conduction. Also, as used herein, convection includes heat transfer through a gaseous medium. Accordingly, heat transfer from air or another gaseous medium in the working volume 112 to the three-dimensional object 102 should be understood to occur primarily through convection. More generally, it should be understood that a description of a primary mode of heat transfer should not be understood to foreclose the possibility of other modes of heat transfer, unless explicitly stated or made clear from the context.

An example of heater 116a,b includes a resistance heater 116a in thermal communication with the media source 106. For example, the resistance heater 116a can be embedded in the media source 106. Heat can be transferred from the resistance heater 116a, through the media source 106, and into the resin 104 carried by the media source 106. Heat transfer from the resistance heater 116a to the resin 104 can occur primarily through conductive heat transfer, and the resistance heater 116a can be controlled to control the temperature and, thus, one or more properties (e.g., flowability) of the resin 104.

In certain implementations, the resistance heater 116a can be additionally, or alternatively, in thermal communication with the build plate 108 such that heat can be transferred (e.g., primarily through conductive heat transfer) from the resistance heater 116a, through the build plate 108, and into the three-dimensional object 102. As compared to a build plate that is not heated, heating the build plate 108 can reduce thermal gradients experienced by the three-dimensional object 102 during fabrication. For example, the temperature of the build plate 108 can be controlled to a temperature substantially similar to a temperature of the media source 106. In instances in which the resistance heater 116*a* heats the build plate 108 and the media source 106, portions of the resistance heater 116*a* heating each of these components can be separately controllable and/or spatially separated as necessary to achieve a desired thermal profile along the media source 106 and the build plate 108.

As an additional, or alternative, example, the heater 116*a,b* can include an ambient heater 116*b* spaced from the media source 106 (e.g., in a portion of the working volume 112 above the media source 106). Spacing of the ambient heater 116 from the media source 106 can be useful, for example, for facilitating separate control of the temperature of a gaseous medium (e.g., air) in the working volume 112 relative to the temperature of the resin 104 carried on the media source 106. The ambient heater 116*b* can be, for example, a forced convection heater, such as a heater including a fan moving air over a heating element, arranged to move heated gas along the portion of the working volume 112 away from the media source 106. In certain implementations, the ambient heater 116*b* can be disposed within the working volume 112 to facilitate efficient heating of the working volume 112. In some implementations, the ambient heater 116*b* can be disposed outside of the working volume 112 and in thermal communication with the working volume 112 through one or more ducts (or similar conduits) to reduce, for example, thermal stress on components of the ambient heater 116*b*.

The heater 116*a,b* can be controllable (e.g., separately controllable from the heat provided to the media source 106) to heat a gaseous medium in a portion of the working volume 112 away from (e.g., above) the media source 106 to a second target temperature. In implementations in which the second target temperature is an elevated temperature (e.g., greater than about 50° C.), heating the gaseous medium in the portion of the working volume away from the media source 106 can maintain the first binder of the resin 104 in a molten state to facilitate, for example, draining the first binder from the three-dimensional object 102 as the three-dimensional object 102 is built through layer-by-layer activation of the second binder of the resin 104. Additionally, or alternatively, heating the gaseous medium in the portion of the working volume away from the media source 106 can be useful for controlling thermal gradients experienced by the three-dimensional object 102 as a portion of the three-dimensional object 102 is near or in contact with the resin 104 at the first target temperature while another portion of the three-dimensional object 102 is away from the resin 104. That is, heating gaseous medium in the portion of the of the working volume away from the media source 106 to the second target temperature can facilitate maintaining the temperature of the three-dimensional object 102 relatively uniform during the fabrication process. This relative thermal uniformity maintained in the three-dimensional object 102 can, for example, reduce warping or other types of deformation that can otherwise occur in the presence of large thermal gradients.

In certain implementations, the second target temperature corresponding to the gaseous medium in the portion of the working volume away from the media source 106 can be the same or about the same (e.g., within about ±5° C.) as the first target temperature of the media source 106 such that the three-dimensional object 102 and the resin 104 carried by the media source 106 are at the same or about the same temperature. In such instances, the repeated introduction and removal of the three-dimensional object 102 into a molten form of the resin 104 can be less likely to create local solidification of one or both of the first binder and the second binder of the resin 104. Because such local solidification can interfere with fabrication of the three-dimensional object 102, maintaining the second target temperature to be about the same as the first target temperature can improve accuracy of the three-dimensional object 102 being formed.

The stereolithography system 100 can include one or more temperature sensors to facilitate controlling the heater 116*a,b* to achieve a desired thermal profile within the working volume 112. For example, the stereolithography system 100 can include a temperature sensor 118 disposed in a portion of the working volume 112 away from the media source 106. The temperature sensor 118 can be, for example, a thermocouple or any one or more of various different types of temperature sensors known in the art and suitable for measuring an indication of temperature in an environment. The heater 116*a,b* can be controllable (e.g., through feedback control) based on a signal received from the temperature sensor 118 to heat the gaseous medium in a portion of the working volume 112 away from the media source 106.

While the working volume 112 can be heated in various different ways to achieve any one or more of the various different advantages described herein, it should be appreciated that certain portions of the stereolithography system 100 can be advantageously thermally isolated from the working volume 112 and/or from the heater 116*a,b*. For example, the activation light source 114 can be thermally isolated from the working volume 112 and/or the heater 116*a,b* to prolong the useful life of the activation light source 114.

In general, the activation light source 114 can deliver light of a wavelength (e.g., a predetermined wavelength) and exposure time suitable to crosslink and/or polymerize one or both of the first binder and the second binder of the resin 104. The activation light source 114 can include an ultraviolet light source in implementations in which the second binder of the resin 104 undergoes crosslinking and/or polymerization upon sufficient exposure to ultraviolet light. As a more specific example, the activation light source 114 can include any one or more of various different ubiquitous light sources that produce light having a wavelength of about 300 nm to about 450 nm (e.g., about 405 nm, which corresponds to the Blu-ray Disc' standard). Further, or instead, the activation light source 114 can produce light within the daylight frequency, and one or both of the first binder and the second binder of the resin 104 can include a daylight curable polymer, such as any daylight curable polymer known in the art.

In certain implementations, the activation light source 114 can have a wavelength greater than the average size of particles suspended in the resin 104, which can reduce the likelihood that the particles will interfere with crosslinking and/or polymerization of one or both of the second binder of the resin 104. Such reduced interference can, for example, advantageously reduce the amount of light exposure time required to crosslink and/or polymerize one or both of the first binder and the second binder in the resin 104. Further, or instead, reduced interference can enhance geometric resolution of the three-dimensional object 102 by reducing light scattering.

The activation light source 114 can be controllable to provide a pattern of light incident on the resin 104. For example, the activation light source 114 can include a laser controlled to rasterize an image on the resin 104. As another, non-exclusive example, the activation light source 114 can include a digital light processing (DLP) projector including a plurality of micromirrors controllable to create an image on the resin 104. As an additional or alternative example, the activation light source 114 can include one or more light emitting diode (LED) displays.

Light from the activation light source 114 can pass through a portion 117 of the media source 106 that is optically transparent to the light from the activation light source 114 such that the presence of the portion 117 of the media source 106 in the light path produces little to no interference with light directed from the activation light source 114 to the resin 104 carried by the media source 106. Thus, for example, in implementations in which the activation light source 114 includes an ultraviolet light source, the portion 117 of the media source 106 in the path of the activation light source 114 can be transparent to ultraviolet light. Further, or instead, in implementations in which the activation light source 114 is disposed outside of the working volume 112, light from the activation light source 114 can pass into build chamber 110 with little to no interference. While the media source 106 and/or the build chamber 110 can be optically transparent to light from the activation light source 114, it should be appreciated that it may be desirable, in certain applications, to use one or both of the media source 106 and the build chamber 110 to filter light from the activation light source 114.

The stereolithography system 100 can include a controller 120 (e.g., one or more processors) and a non-transitory, computer readable storage medium 122 in communication with the controller 120 and having stored thereon computer executable instructions for causing the one or more processors of the controller 120 to carry out the various methods described herein. For example, the controller 120 can be in communication with one or more of the build plate 108, the activation light source 114, the heater 116a,b, and the temperature sensor 118 to control fabrication of the three-dimensional object 102 based on a three-dimensional model 124 stored on the computer readable storage medium 122. In certain instances, the stereolithography system 100 can further include a camera and vision system that can detect parameters (e.g., dimensions) of the three-dimensional object 102 as it is formed, and the computer-readable storage medium 122 can store a digital twin 126 of the three-dimensional object 102 such that variations and defects of the three-dimensional object 102 can be evaluated.

In general, the resin 104 can be responsive to light, heat, or a combination thereof controlled by the controller 120 such that one or both of the first binder and the second binder can be controllably handled and modified. As a specific example, the controller 120 can control heat to facilitate spreading the resin 104 along the media source 106 and, further or instead, can control light along the media source to control a two-dimensional pattern of crosslinking, polymerization, or both, in one or more of the first binder and the second binder of the resin 104. The ability to control accurately the distribution of the resin 104 and crosslinking or polymerization of one or both of the first binder and the second binder of the resin 104 can advantageously facilitate controlling a shape of a layer and, thus, controlling dimensional features of the three-dimensional object 102 during a stereolithography process.

The resin 104 can include particles suspended in a mixture of the first binder and the second binder. Thus, more specifically, the particles can be suspended in a solution including the first binder and the second binder. In general, the particles can be thermally processable to coalesce with one another, and optionally with additional material, into a mass. In general, the mass formed through coalescence of the particles can be denser than the resin and, thus, can include a porous mass or a solid mass. As used herein, thermal processing shall be understood to include any manner and form of coalescence of the particles based on direct or indirect application of heat. Examples, therefore, of thermal processing include sintering, infiltration with liquid metal, and thermally-activated pyrolysis of a polymer-derived ceramic. Further, in instances in which thermal processing includes sintering, such thermal processing shall be understood to include one or more of pre-sintering, solid state sintering, liquid phase sintering, transient liquid phase sintering, and, more generally, any manner and form of sintering known in the art.

At least one of the first binder and the second binder can be reactive to crosslink or polymerize upon sufficient exposure of the first binder and the second binder to a predetermined wavelength of light from the activation light source 114. Such crosslinking or polymerization can, for example, increase the resistance of the respective binder to deformation. That is, crosslinking or polymerizing at least one of the first binder and the second binder can facilitate maintaining a shape of the three-dimensional object and, accordingly, can improve reduce the likelihood of unintended deformation of the three-dimensional object as the three-dimensional object undergoes post-processing to form a finished part.

In certain implementations, the first binder and the second binder can each be separately extractable from a coalesced mass of the particles forming the three-dimensional object 102. That is, the first binder can be removable from the particles through a first debinding process, and the second binder can be removable from the particles through a second debinding process, which can be different from the first debinding process and/or temporally separate from the first debinding process.

The physical properties of the first binder and the second binder can be changed through a selective and controlled application of energy (e.g., light, heat, or a combination thereof) during a stereolithographic process to address different requirements associated with different stages of the stereolithographic process, such as handling (e.g., spreading) the resin 104, forming the three-dimensional object 102 layer-by-layer, and finishing the three-dimensional object 102 into a dense part formed primarily of the particles. For example, as described in greater detail below, the first binder and the second binder can have different melt temperatures to facilitate, among other things, decoupling spreading characteristics of the resin 104 from binding characteristics of the resin 104. Additionally, or alternatively, the first binder and the second binder can have different responses to incident light. That is, continuing with a more specific example, the first binder can be substantially non-reactive under exposure to wavelengths of light sufficient to crosslink or polymerize the second binder such that the physical properties of the second binder can be changed during a stereolithographic process without significantly changing the physical properties of the first binder.

The suspension of particles in the resin 104 can include a dispersion of particles in a solid or a molten form of a mixture of the first binder and the second binder. The dispersion of the particles can be uniform or substantially uniform (e.g., varying by less than about ±10 percent) within the mixture of the first binder and the second binder. More generally, however, the degree of uniformity of the particles can be a function of strength and/or design tolerances acceptable for the fabrication of a finished part formed from the three-dimensional object 102.

The first binder and the second binder can be, for example, miscible with one another such that the mixture of the first binder and the second binder is homogenous. Alternatively, the first binder and the second binder can be immiscible with one another. In such instances, the dispersion of the particles in the mixture of the first binder and the second binder can be formed or made more homogeneous by shaking or otherwise agitating a molten form of the resin 104 prior to or during a stereolithography process.

One or both of the first binder and the second binder can be a low molecular weight material (e.g., a monomer or an oligomer), with the low molecular weight indicative of a low degree of crosslinking or polymerization. For example, one or both of the first binder and the second binder can have a molecular weight of less than about 1000 g/mol. Continuing with this example, the molecular weight of the respective binder can be increasable from less than about 1000 g/mol to greater than about 1000 g/mol (e.g., greater than about 2000 g/mol) under exposure to the predetermined wavelength of light sufficient to crosslink or polymerize the second binder. The resulting crosslinking or polymerization associated with such an increase in molecular weight of the respective binder can correspond to curing of the respective binder such that the resin 104 in a respective layer takes a relatively stable shape during fabrication of the three-dimensional object 102.

The first binder and the second binder can have different melt temperatures to facilitate handling the resin 104 in certain implementations. For example, the first binder can have a first melt temperature and the second binder can have a second melt temperature less than or about equal to the first melt temperature. In such instances, the flow of the resin 104 can be controlled by controlling temperature of the resin 104 relative to the melt temperature of the first binder. As a more specific example, the first binder can have a first melt temperature less than about 80° C., and the temperature of the media source 106, the build plate 108, and/or the working volume 112 can be controlled to be above about 80° C. such that the resin 104 is molten prior to receiving incident light from the activation light source 114. Additionally, or alternatively, the first binder can have a melt temperature above about 25° C. such that the resin 104 can be substantially solid (e.g., in the form of a paste) to facilitate storing the resin 104 in a stable form—with the particles suspended in the first binder and the second binder—for a significant period of time, such as multiple weeks or longer. In certain implementations, the concentration of the particles suspended in the mixture of the first binder and the second binder can be such that the resin 104 is a non-Newtonian fluid at 25° C.

Additionally, or alternatively, the first binder and the second binder can have different decomposition temperatures. For example, the first binder can have a first decomposition temperature, and the second binder can have a second decomposition temperature greater than the first decomposition temperature such that the second binder can generally withstand heating to a greater temperature. For example, the second binder can remain in the three-dimensional object 102 as the three-dimensional object 102 is heated further, after the first binder is thermally debound from the three-dimensional object 102 through a primary debinding process.

In general, the first binder can be extractable from the second binder and/or the material of the particles forming the three-dimensional object 102 through a primary debinding process, which can include any of various different processes suited to the composition of the first binder and compatible with separately extracting the second binder from the three-dimensional object 102 through a secondary debinding process. For example, the first binder can include a wax extractable from the second binder by chemical solvation in a non-polar chemical following exposure of the second binder to wavelengths of light sufficient to crosslink or polymerize the second binder. As another, non-exclusive example, the first binder can include a plurality of low-molecular weight constituents (e.g., paraffin wax and steric acid), each constituent extractable from the second binder by the same chemical solution (e.g., hexane) following exposure of the second binder to wavelengths of light sufficient to crosslink or polymerize the second binder. Additionally, or alternatively, the first binder can include polyethylene glycol extractable from the second binder by dissolution by water or alcohols following exposure of the second binder to wavelengths of light sufficient to crosslink or polymerize the second binder. Still further in addition, or in the alternative, the first binder can include a wax extractable from the second binder by supercritical carbon dioxide fluid following exposure of the second binder to wavelengths of light sufficient to crosslink or polymerize the second binder. Yet further in addition, or yet further in the alternative, the first binder can include a low molecular weight polyoxymethylene extractable from the second binder by catalytic debinding in nitric oxide vapor. For example, the polyoxymethylene can melt at a temperature substantially similar to a temperature at which the second binder is photopolymerizable. In certain implementations, the first binder can include polyanhydride extractable from the second binder by hydrolysis and dissolution in aqueous solution following exposure of the second binder to wavelengths of light sufficient to crosslink or polymerize the second binder. In some implementations, the first binder can include a wax thermally extractable from the second binder following exposure of the second binder to wavelengths of light sufficient to crosslink or polymerize the second binder. The thermal extraction can include, as an example, boiling the wax at a temperature at which the second binder remains substantially intact (e.g., substantially retaining its shape) in the three-dimensional object 102.

The second binder can be removable from the first binder and/or from the material of the particles forming the three-dimensional object 102 through a secondary debinding process, which can include any of various different processes suited to the composition of the second binder. For example, the second binder can be debindable from the three-dimensional object 102 by cleaving and/or un-polymerizing the second binder (e.g., through one or more of hydrolyzing or solvolyzing) following crosslinking or polymerization of the second binder. As a more specific example, the second binder can include acetal diacrylate, which can be extractable from the first binder by catalytic debinding in nitric oxide vapor following exposure of the second binder to a wavelength of light sufficient to crosslink or polymerize the second binder. As an additional or alternative example, the second binder can include anhydride diacrylate, which can be extractable from the first binder by hydrolysis and dissolution in one or more aqueous solutions following exposure of the second binder to the wavelength of light sufficient to crosslink or polymerize the second binder. Yet further in addition, or further in the alternative, the second binder can include a saccharide diacrylate (e.g., monosaccharide diacrylate, disaccharide diacrylate, or a combination thereof), each of which can be extractable from the first binder by hydrolysis in one or more aqueous solutions including a catalyst (e.g., a catalyst including one or more biological enzymes, such as amylase) for hydrolysis of the crosslinked or polymerized second binder following exposure of the second binder to the wavelength of light sufficient to crosslink or polymerize the second binder. Additionally, or alternatively, in instances in which the second binder is debindable by cleaving and/or un-polymerizing the second binder, the first binder can have a high molecular weight (e.g., greater than about 1000 g/mol) and be present in a small volume percentage (e.g., less than about 10 percent) in the resin 104.

In certain implementations, the first binder and the second binder both can be crosslinked or polymerized through sufficient exposure to light of a predetermined wavelength. In such implementations, the primary debinding process associated with extracting the first binder from the second binder and/or from the material of the particles forming the three-dimensional object 102 can include breaking down the crosslinked or polymerized first binder while the second binder remains cross-linked or polymerized in the three-dimensional object 102. As a specific example, the primary debinding process can include applying a catalytic solution to the three-dimensional object to cause part of the first binder to depolymerize, dissolve, or otherwise breakdown. An example of a first binder that can react to light and can be subsequently broken down in this way include anhydride and methacrylic anhydride. More generally, the first binder that can be broken down in this way can include a small molecule with two acylate groups (a diacrylate) containing one or more anhydride linkages. Continuing with this example, the acrylates can polymerize upon exposure to ultraviolet light, and the anhydride linkages can break down in the presence of water and other molecules.

The particles suspended in the resin 104 can include, for example, any one or more of various different metals. Further, or instead, the particles can include any one or more of various different ceramics. To facilitate producing a solid part with substantially uniform strength characteristics along the part, the particles can have the same composition. Additionally, or alternatively, the particles have a substantially uniform size. In certain implementations, the particles can include nanoparticles (e.g., particles having an average particle size of greater than about 1 nanometer and less than about 100 nanometers). The nanoparticles can facilitate thermally processing the three-dimensional object 102 to form a finished part. As a specific example, the nanoparticles can facilitate sintering the three-dimensional object 102 at a lower temperature.

In certain instances, the particles can have an average size less than a wavelength of light sufficient to crosslink or polymerize one or both of the first binder and the second binder, which can have any of various different advantages described herein. For example, such a ratio of particle size to the wavelength of light can reduce the likelihood that particles in the resin 104 will interfere with the incident light, which can result in shorter times associated with crosslinking or polymerizing one or both of the second binder. This reduction in time can, in turn, reduce the time associated with forming a finished part, which can be particularly useful for mass production of parts.

In certain instances, it can be desirable to have a high concentration of the particles in the resin 104 and, thus, a comparatively lower concentration of the first binder and the second binder in the resin 104. A high concentration of the particles in the resin 104 can, for example, reduce the amount of the first binder and/or the second binder in the resin 104, therefore reducing the time and/or energy required to crosslink or polymerize one or both of the first binder and second binder in the resin 104. Additionally, or alternatively, a high concentration of the particles in the resin 104 can reduce the amount of each of the first binder and the second binder in the resin 104, which can reduce the amount of time required for extracting the first binder and the second binder from the three-dimensional object 102. As a specific example of a high concentration, the concentration (by volume) of the particles in the resin 104 can be within ±25 percent of the tap density of the particles. As used herein, the tap density of particles is the bulk density of a powder of the particles after a compaction process specified in ASTM B527, entitled "Standard Test Method for Tap Density of Metal Powders and Compounds," the entirety of which is incorporated herein by reference.

In some implementations, the particles in the resin 104 can include modified surfaces. With these modified surfaces, the particles can exhibit one or more physicochemical characteristics that differ advantageously from the corresponding one or more physicochemical characteristics of the underlying material of the particles. For example, the particles can include chemically functionalized surfaces such as surfaces having a metal oxide coating useful for resisting corrosion or other undesired chemical reactions. Additionally, or alternatively, the particles can include functional groups useful for resisting settling of the particles in a mixture of the first binder and the second binder through steric hindrance. In certain instances, under ambient conditions (e.g., in air at about 25° C. at atmospheric pressure and with relative humidity of 20-80%), the particles suspended in the mixture of the first binder and the second binder in the resin 104 can have a timescale of settling of greater than about two weeks, which can facilitate storing the resin 104 in a stable form for a useful period of time. In some instances, the settling time of the particles in the resin 104 can be greater than the amount of time at which the first binder is molten during the stereolithography process to reduce the likelihood of unintended settling of the particles as the three-dimensional object 102 is formed.

The resin 104 can, further or instead, include one or more of a photo-absorber (e.g., a Sudan dye) or a photo-initiator suspended in the mixture of the first binder and the second binder. Inclusion of one or more of a photo-absorber or a photo-initiator can facilitate, for example, tuning the resin 104 to achieve a particular response (e.g., a target curing time for one or more of the first binder or the second binder) upon exposure to activation light from the activation light source 114.

The volumetric composition of the resin 104 can be a function of, among other things, the composition of the constituent components of the resin 104. In certain implementations, the second binder can be about 10 percent to about 50 percent by volume of the total volume of the resin 104. The first binder can include, for example, one or more of the following: paraffin wax, carnauba wax, stearic acid, polyethylene glycol, polyoxymethylene, oleic acid, and dibutyl phthalate. The second binder can include, for example, one or more of the following: poly(methyl methacrylate), polyethylene glycol diacrylate, urethane oligomers functionalized to acrylate groups, epoxy oligomers functionalized to acrylate groups, 1,6-Hexanediol acrylates, or styrene. Additionally, or alternatively, the resin 104 can include one or more of the following mixed with the first binder, the second binder, and the particles: ethylene vinyl acetate, a slip agent (e.g., stearic acid), and/or a compatibilizer (e.g., metal stearate (e.g., zinc stearate), stearic acid, or a combination thereof). In an exemplary formulation, the first binder can include polyethylene glycol and the second binder can include poly(methyl methacrylate). For example, polyethylene glycol can be about 40-90 percent of the combined weight of the first binder and the second binder and poly(methyl methacrylate) can be about 10-60 percent of the combined weight of the first binder and the second binder. In another exemplary formulation, the first binder can include paraffin wax and the second binder can include a waxy or hydrophobic diacrylate oligomer.

Figure 2:
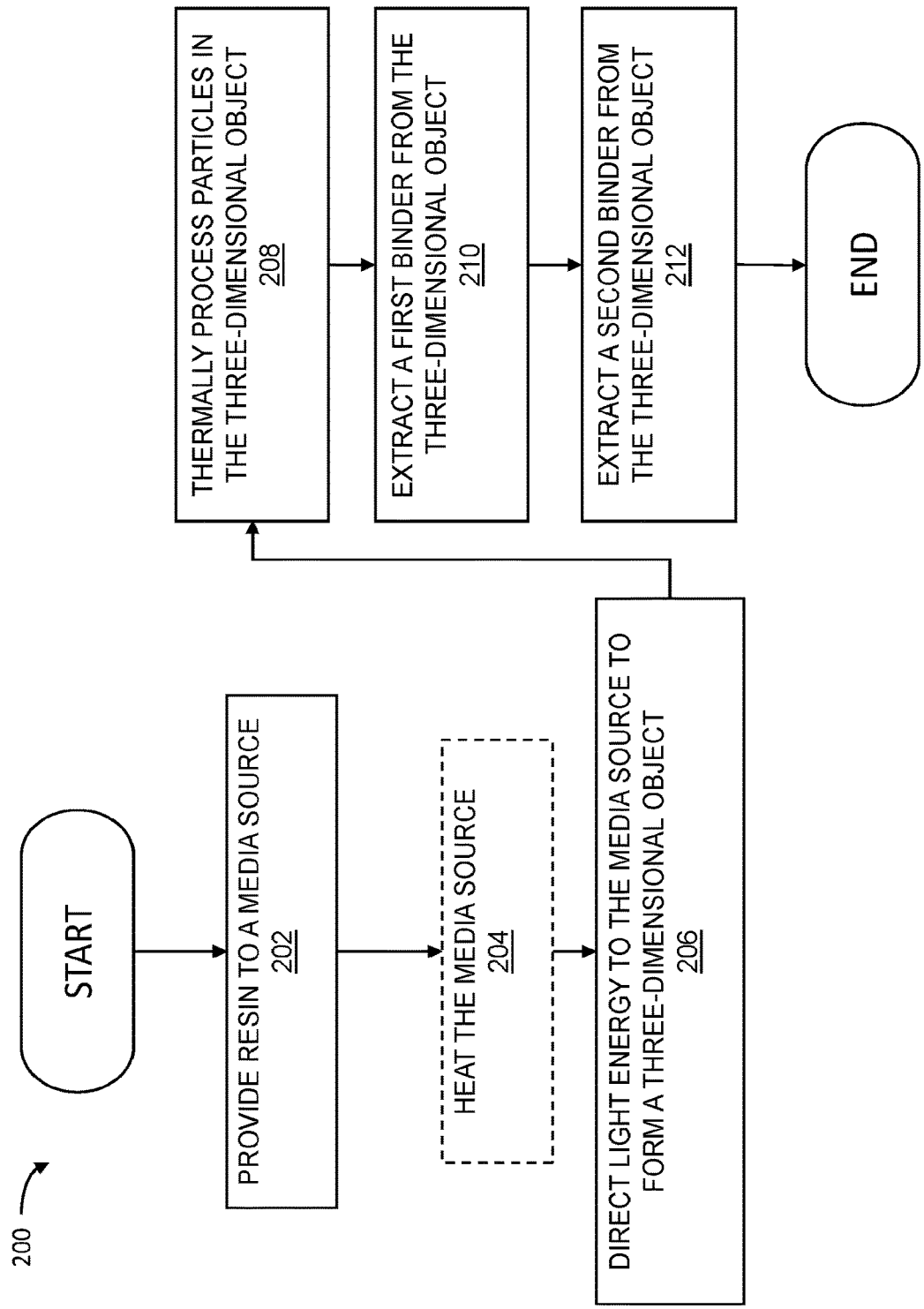
FIG. 2 is a flow chart of an exemplary method of fabricating a three-dimensional object through stereolithography.

FIG. 2 is a flowchart of an exemplary method 200 of fabricating a three-dimensional object using any one or more of the various different stereolithography systems described herein. For example, the exemplary method 200 can be implemented as computer-readable instructions stored on the computer-readable storage medium 122 (FIG. 1) and executable by the controller 120 (FIG. 1) to operate the stereolithography system 100 (FIG. 1) to form the three-dimensional object 102 (FIG. 1).

As shown in step 202, the exemplary method 200 can include providing a resin to a media source. The media source can be, for example, disposed within a working volume defined by a build chamber. Further, or instead, the resin can be any of the various different resins described herein and, thus, can include particles suspended in a mixture of a first binder and a second binder.

Providing the resin to the media source can include depositing the resin on the media source. For example, the resin can be moved through a dispensing section, such as a nozzle, of the media source, and the dispensing section can be, optionally, heated to a temperature greater than the melt temperature of the first binder of the resin such that the resin becomes molten to facilitate flow through the dispensing section and spreading along the media source. Providing the resin to the media source can additionally, or alternatively, include moving a solid feedstock of the resin into a working volume of the stereolithography system. For example, the feedstock can be moved into the working volume from a storage container thermally isolated from the working volume. Such thermal isolation can be useful, for example, for maintaining the feedstock in a solidified form such that the particles of the resin can remain suspended for a substantial period of time. More generally, providing the resin to the media source can include moving the resin with any one or more of the fabrication systems described herein, such as any one or more of the fabrication systems described below.

Providing the resin can include dispersing the resin to form a layer of resin on a substrate. The thickness of the layer of resin can represent the resolution of the stereolithography process and, thus, a small layer thickness can be useful for fabricating parts with a high degree of spatial resolution (e.g., fewer errors). Also, or instead, a small layer of thickness can be useful for increasing the likelihood that activation light can sufficiently penetrate the layer to activate at least one of the first binder and the second binder along the depth of the layer. In certain implementations, the layer of the resin can be, for example, less than about 200 μm.

As shown in step 204, the exemplary method 200 can, optionally, include heating the media source to a first target temperature. The first target temperature can be greater than a melt temperature of a first binder (e.g., greater than about 50° C.). It should be understood that heating the media source to the first target temperature can be useful for maintaining the resin in a molten form, which can facilitate spreading the resin along the media source. Heating the media source can include any of the various different heating methods described herein and, thus, can include conductively heating the media source (e.g., through a resistance heater in contact with or embedded in the media source).

In certain implementations, the exemplary method 200 can additionally, or alternatively, include heating a gaseous medium in a portion of the working volume away from the media source to a second target temperature (e.g., greater than about 50° C.) according to any of the various different methods described herein. The light energy can be directed in a predetermined pattern onto a layer of resin with the air in the portion of the working volume away from the media source at the second target temperature, which can be useful for reducing thermal gradients in the three-dimensional object being fabricated, as described herein.

As shown in step 206, the method can include directing light energy to the media source. For example, the light energy can be directed to the media source with the media source at the first target temperature and, thus, with the first binder in a molten state. The light energy can be received from any of the various different activation light sources described herein and, therefore, can include light energy in or near the ultraviolet range.

The light energy can be directed to the media source, and thus to the resin, in a predetermined pattern corresponding to dimensions received from a three-dimensional model forming the basis of the three-dimensional object being fabricated. The light energy can be made incident on the media source, and thus on the resin, for a time sufficient for at least one of the first binder and the second binder to undergo modification, such as any one or more modifications described herein. Further or instead, the step 206 of directing light energy can be repeated as necessary to direct light energy onto each layer of a plurality of layers of the resin to cure the resin on a substrate carried by the build plate. The light energy can be directed onto the resin in a respective predetermined pattern associated with the respective layer to form the three-dimensional object.

As shown in step 208, the exemplary method 200 can include thermally processing particles in the three-dimensional object according to any one or more of the thermal processes described herein. Thus, thermally processing the particles can include any manner and form of applying heat to densify the three-dimensional object (e.g., with the densification including coalescence of the particles with one another and, optionally with one or more other materials, to form a mass). For example, thermally processing the particles in the three-dimensional object can include sintering the particles. Further, or instead, thermally processing the particles in the three-dimensional object can include infiltrating the three-dimensional object with a liquid metal. Still further or instead, thermally processing the particles in the three-dimensional object can include thermally-activated pyrolysis of a polymer-derived ceramic. In general, thermally processing the particles can be carried out in a post-processing station, as described in greater detail below.

As shown in step 210, the exemplary method 200 can include extracting a first binder from the three-dimensional object. The extraction of the first binder from the three-dimensional object can be carried out in a primary debinding step that leaves substantially all of the second binder and the material of the particles remaining in the three-dimensional object. The primary debinding process can include any one or more debinding processes known in the art and, therefore, can include one or more of thermal debinding and chemical debinding (which can include catalytic debinding), as appropriate based on the composition of the first binder.

Figure 3:
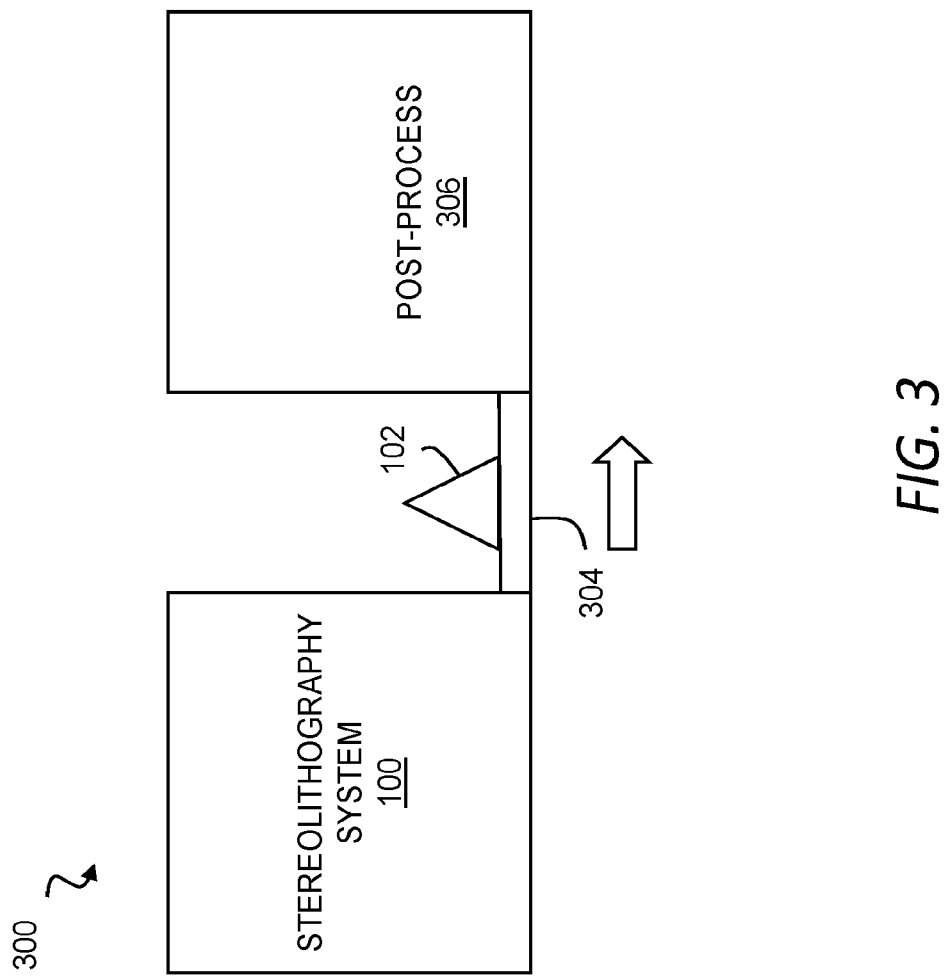
FIG. 3 shows an additive manufacturing system for use with the stereolithography system of FIG. 1.

Referring now to FIGS. 1 and 3, an additive manufacturing system 300 can include the stereolithography system 100, a conveyor 304, and a post-processing station 306. In use, the three-dimensional object 102, in the form of a green part, can be moved along the conveyor 304 and into the post-processing station 306, where the first binder and the second binder can be extracted from the three-dimensional object 102 and/or where the three-dimensional object 102 can undergo thermal processing to form a final part. As an example, the three-dimensional object 102 can undergo one or more of thermal debinding and chemical debinding to remove the first binder and the second binder from the three-dimensional object 102.

In certain implementations, the three-dimensional object 102 can undergo one or more thermal processes in the post-processing station 306. For example, the three-dimensional object 102 can be sintered in the post-processing station 306. In addition to densifying the three-dimensional object 102, sintering can alter chemical properties of the particles, which can be useful for transforming certain types of particles to a metal or to an additive in a metallic alloy in the finished part. Further, or instead, thermally processing the three-dimensional object 102 in the post-processing station 306 can include infiltrating the three-dimensional object 102 with a liquid metal. The infiltration of the liquid metal into the three-dimensional object 102 can include, for example, movement of the liquid metal into spaces in the three-dimensional object 102 through wicking. In some instances, infiltrating the three-dimensional object 102 with the liquid metal can include replacing the first binder and the second binder with the liquid metal. Additionally, or alternatively, thermally processing the three-dimensional object 102 can include thermally activated pyrolysis of a polymer-derived ceramic (e.g., as described in greater detail below with respect to FIG. 16).

While the post-processing station 306 is shown as being separate from the stereolithography system 100, it should be appreciated that some or all of the post-processing station 306 can be incorporated into the stereolithography system 100 such that any one or more of post-processing steps described herein can occur in the stereolithography system 100.

While certain embodiments have been described, other embodiments are additionally or alternatively possible.

Figure 4:
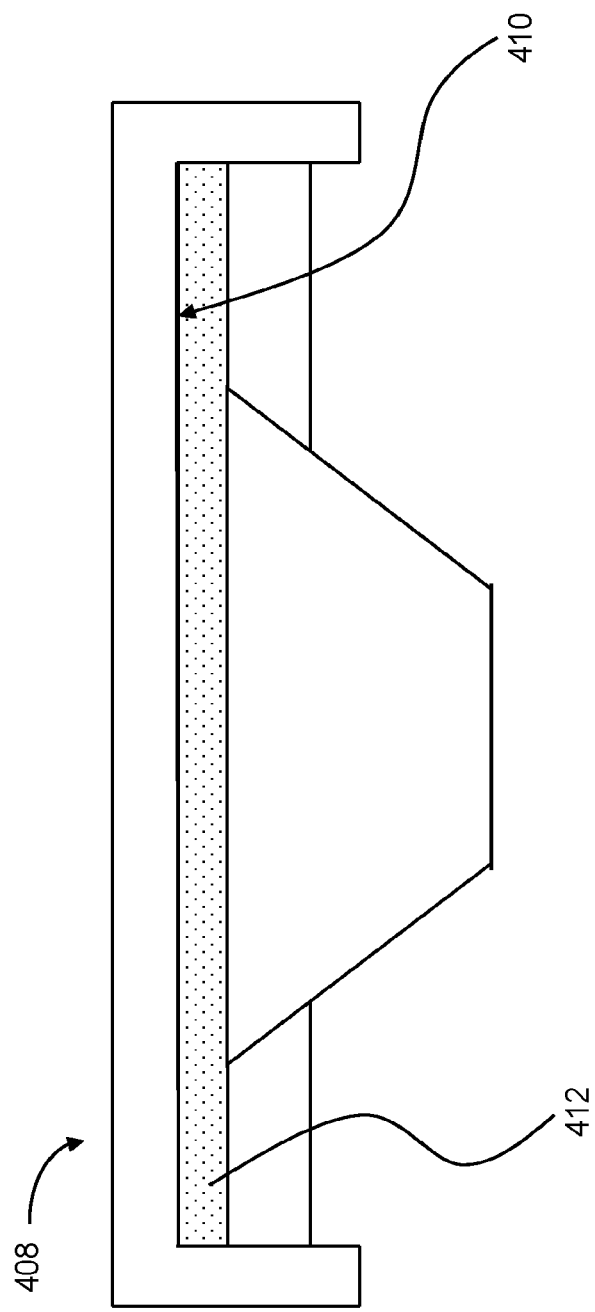
FIG. 4 is a close-up view of a build plate of a stereolithography system.

For example, while a build plate has been described, it should be appreciated that the build plate of any of the various different stereolithography systems described herein can include additional or alternative features. For example, referring now to FIG. 4, a build plate 408 can be useful for reducing errors in fabricating three-dimensional objects. Unless otherwise specified or made clear from the context, the build plate 408 should be understood to be interchangeable with the build plate 108 (FIG. 1) for use in the stereolithography system 100.

The build plate 408 can include a build surface 410 and a coating 412 disposed along the build surface 410. The coating 412 can be adherable to any of the various different resins described herein (e.g., the resin 104 in FIG. 1). For example, the coating 412 can be adherable to the resin following exposure of the resin to light sufficient to crosslink and/or polymerize one or both of the first binder and the second binder. Thus, continuing with this example, the coating 412 can be adherable to a three-dimensional object being formed on the build surface 410 (e.g., the three-dimensional object 102 of FIG. 1). Further, or instead, the resin can be preferentially adherable to the coating 412 on the build surface 410 over adherence to a media source (e.g., the media source 106 in FIG. 1), increasing the likelihood that the resin will tend to move with the build plate 408 as the build plate 408 is moved away from the media source. Accordingly, as compared to a system without a coating, the coating 412 can reduce the likelihood of fabrication errors that would otherwise result from improper or insufficient adherence of the resin to the build plate 408.

The coating 412 can include, for example, a first binder, a second binder, or a combination thereof to facilitate adhering the resin including the first binder and the second binder to the coating 412. More specifically, the coating 412 can include the first binder, the second binder, or a combination thereof, and can be substantially free of the particles of the resin to further improve adhesion between the coating 412 and the resin used for a particular stereolithography fabrication.

The coating 412 can be provided to the build surface 410 from a coating source at the start of a new build, such as before a first layer of a three-dimensional object is formed on the build plate 408. For example, the coating source can include a film of the coating 412 positionable on the build surface 410 at the start of a new build. Additionally, or alternatively, the coating source can include a reservoir of the coating 412, from which the coating 412 can be drawn and delivered (e.g., through a nozzle) to the build surface 410. Further, or instead, the coating can be manually positioned on the build surface 410 as part of a set-up process.

Figure 5:
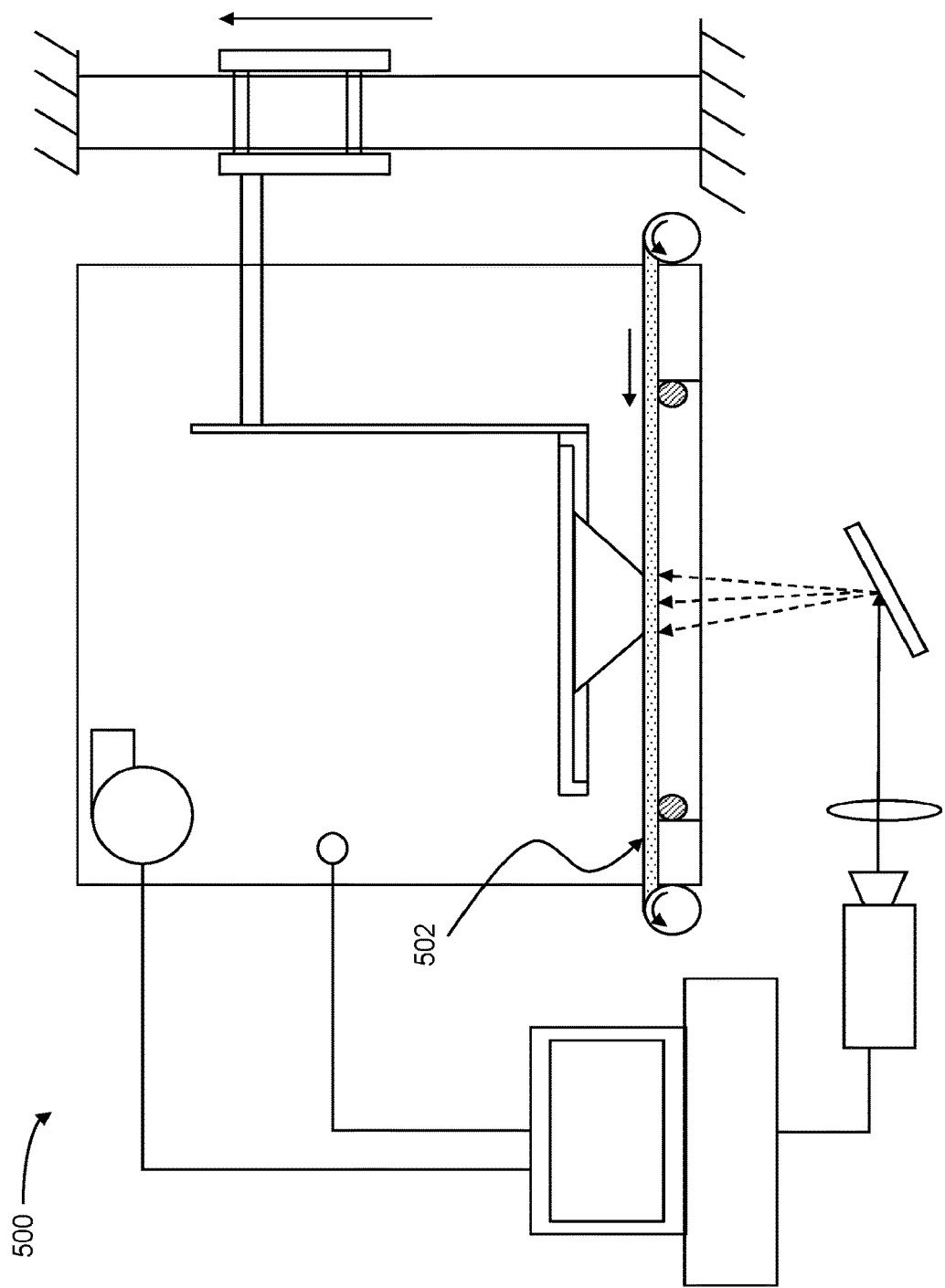
FIG. 5 is a schematic representation of a stereolithography system.

As another example, while stereolithographic systems have been described as including certain modes of delivery of a resin to a media source, other delivery modes are additionally or alternatively possible. For example, referring now to FIG. 5, a stereolithography system 500 is analogous to the stereolithography system 100 (FIG. 1), except as described below or made clear from the context. The stereolithography system 500 can include a film 502 movable within a working volume to move resin to a media source, where incident light from an activation light source can activate a binder in the resin to form a layer of a three-dimensional object. Examples of materials that can be used to form the film 502 include, but are not limited to: polypropylene, polytetrafluoroethylene, and polydimethylsiloxane. More generally, the film 502 can be substantially transparent to activation light used to crosslink or polymerize one or both of the first binder or the second binder such that the film 502 can be disposed between an activation light source and the resin without interfering with activation of the first binder and/or the second binder in the resin.

In certain implementations, the film 502 can be indexed to provide a new layer of the resin along the media source at the beginning of the build of each layer. For example, between each layer, the film 502 can be indexed according to a dimension of the media source. Additionally, or alternatively, the film 502 can be dynamically indexed such that an area of the film 502 corresponding to resin used in an immediately preceding layer is moved beyond the media source prior to building an immediately subsequent layer. Further, or instead, dispersing the resin can additionally or alternatively include the use of a roll-to-roll configuration in which a roll of the resin is brought into contact with a roll of the film 502 such that the resin becomes dispersed on the film 502.

Figure 6:
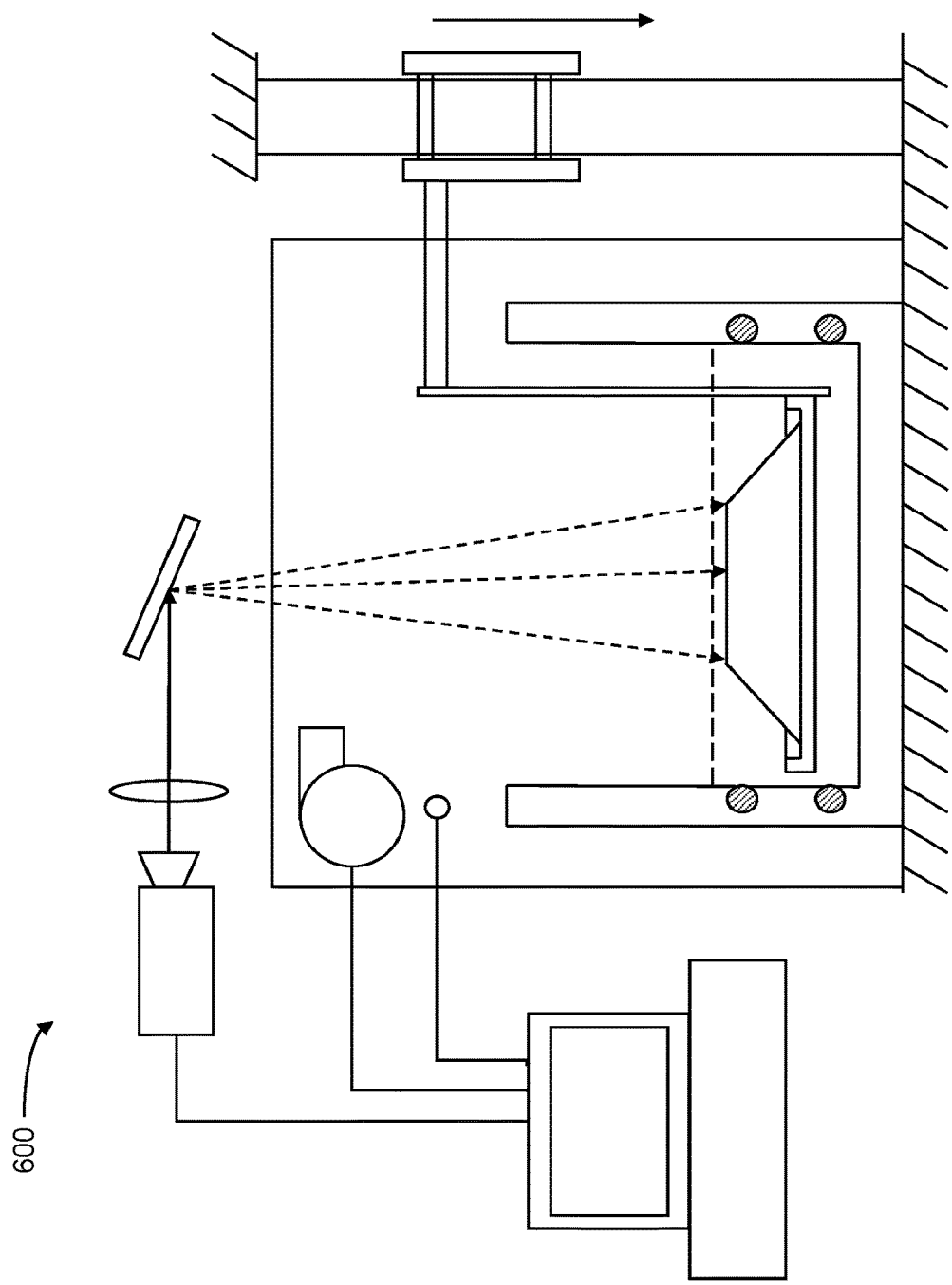
FIG. 6 is a schematic representation of a stereolithography system.

As still another example, while stereolithographic systems have been described as being inverted, additional or alternative configurations are possible. For example, referring now to FIG. 6, a stereolithography system 600 is analogous to the stereolithography system 100 (FIG. 1), except as described below or made clear from the context. The stereolithography system 600 can be oriented such that a build plate moves downward, into a media source, as a three-dimensional object is formed layer-by-layer.

As yet another example, stereolithographic systems can additionally, or alternatively, include configurations for shearing discrete portions of each layer of a three-dimensional object being formed. For example, light energy can be delivered to discrete portions of any one or more of the resins described herein to cure the resin, and the cured resin in the respective discrete portion can be sheared independently of shearing the cured resin in other discrete portions. As used herein, a "cured resin" shall be understood to be a resin, such as any one or more of the resins described herein, including at least one cured binder and may additionally include one or more uncured binders.

In general, a layer of a resin carried on a media source can be cured between the media source and a substrate carried on a build plate of a stereolithographic system, with the layer of the cured resin adhering to both the substrate and the media source. Before a subsequent layer of the resin can be deposited on top of the current layer of cured resin, the current layer of the cured resin is separated from the media source. As a specific example, the current layer of the cured resin can be separated from the media source through the application of a shear force between the media source and the current layer. In general, however, resins loaded with particles, such as described herein, can decrease the shear strength of the cured resin and, thus, can have an adverse impact on proper separation of the cured binder from the media source. Thus, to reduce the likelihood of improper separation in a cured binder loaded with particles, stereolithographic systems of the present disclosure can separate discrete portions of each layer of cured resin from the media source. As compared to separating an entire layer of a cured resin from a media source, separating discrete portions of each layer of the cured resin from the media source can facilitate complete separation of the cured resin from the media source, which can correspondingly improve accuracy of the three-dimensional object formed through successively building layers of the cured resin on top of one another.

Figure 7A:
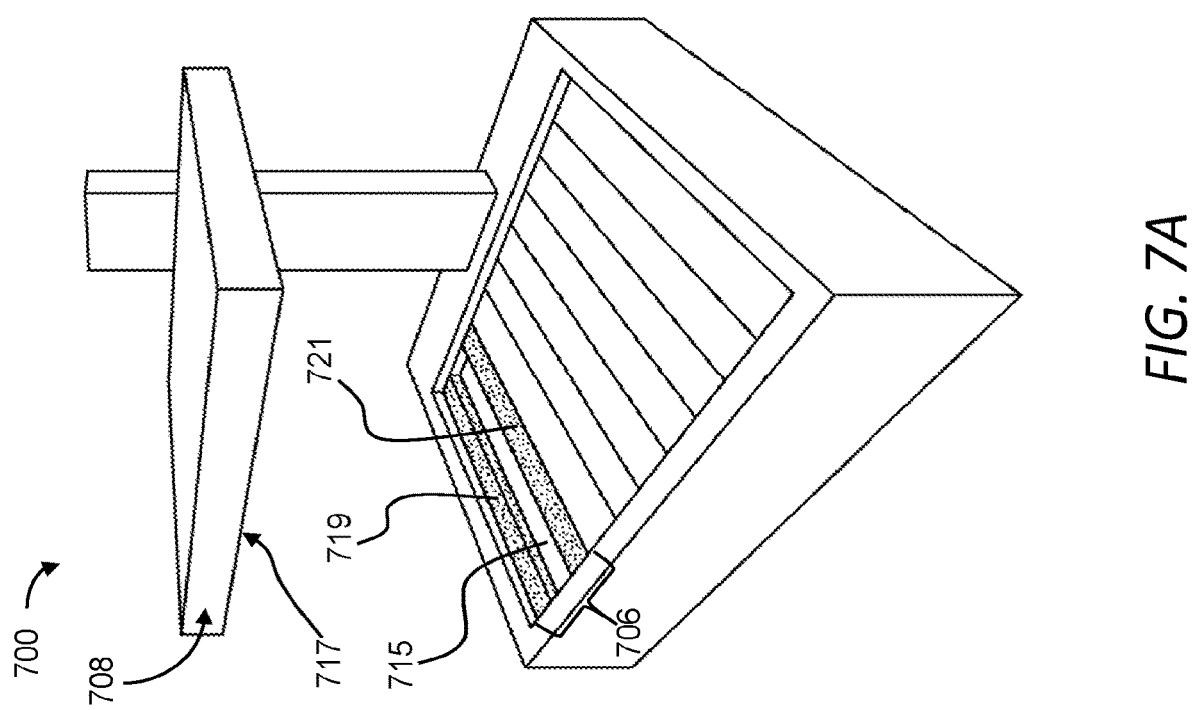
FIG. 7A is a schematic representation of a fabrication system of a stereolithography system.
Figure 7B:
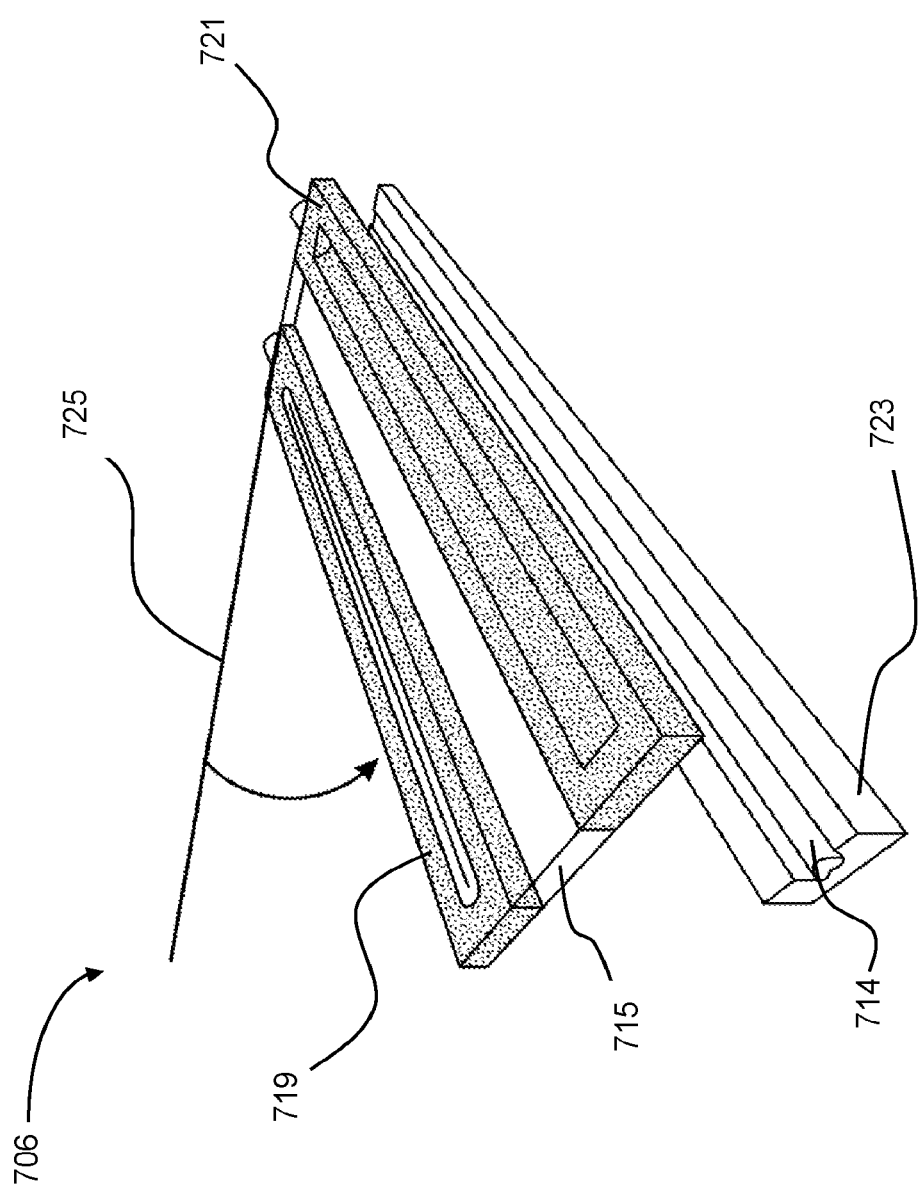
FIG. 7B is an exploded view of a portion of the fabrication system of FIG. 7A.

Referring now to FIGS. 7A and 7B, a fabrication system 700 can include a media source 706, a build plate 708, and an activation light source 714. Unless otherwise specified or made clear from the context, the fabrication system 700 can be part of any one or more of the stereolithography systems described herein. Thus, for example, the fabrication system 700 can be part of the stereolithography system 100 (FIG. 1), with media source 706 and the build plate 708 of the fabrication system 700 disposed in the working volume 112 defined by the build chamber 110.

The activation light source 714 can be, for example, any one or more of the activation light sources described herein. Thus, by way of example and not limitation, the activation light source can include a light source having a wavelength of about 300 nm to about 350 nm.

The media source 706 can include a transparent portion 715. The activation light source 714 can be positioned to direct activation light into a working volume (e.g., the working volume 112 in FIG. 1) through the transparent portion 715 of the media source 706 toward a surface 717 of the build plate 708. In use, as described in greater detail below, the activation light can selectively cure discrete portions of a layer of a resin on a substrate (e.g., the surface 717 of the build plate 708 or a previous layer) carried by the build plate 708 in the working volume. As also described in greater detail below, one or both of the build plate 708 and the transparent portion 715 of the media source 706 can be movable relative to one another. The movement of the build plate 708 and the transparent portion 715 of the media source 706 relative to one another can, for example, change an origin of a shear force on a cured resin between the build plate 708 and the media source 706.

As an example, one or both of the build plate 708 and the transparent portion 715 of the media source 706 can be movable relative to one another to change a position of the transparent portion 715 of the media source 706 by an increment substantially equal to a width of the transparent portion 715 of the media source 706 in a direction parallel to the surface 717 of the build plate 708. Through such incremental movement of the transparent portion 715 of the media source 706, the transparent portion 715 of the media source 706 can be moved in adjacent incremental steps in a direction parallel to the surface 717 of the build plate 708. As the transparent portion 715 of the media source 706, light energy from the activation light source 714 can cure a layer of the resin in discrete portions. More specifically, in a first increment, the light energy from the activation light source 714 can cure a first discrete portion of the layer of resin, in a second increment adjacent to the first increment, the light energy from the activation light source 714 can cure a second discrete portion of the layer of resin, and so forth.

The transparent portion 715 of the media source 706 can, for example, span a dimension of the build plate 708. In certain instances, the transparent portion 715 of the media source 706 can be movable in a direction transverse to (e.g., substantially perpendicular to) the spanned dimension of the surface 717 of the build plate 708. Additionally, or alternatively, the width of the transparent portion 715 of the media source 706 can be less than a dimension of the build plate 708 in the direction of the changed position of the transparent portion 715 of the media source 706 such that a layer of the resin can be cured in multiple discrete portions. Advantageously, each discrete cured portion of the layer of the resin can be separated from the transparent portion 715 (e.g., through the application of a shear force) before the transparent portion 715 is moved to the next position and the next discrete portion of the layer of the resin is cured. In certain implementations, the light energy from the activation light source 714 can be directed to discrete portions of a given layer of the resin as the activation light source 714 moves substantially continuously across the given layer of the resin. Similarly, shear force can be applied to the discrete cured portions of the resin in a substantially continuous manner. In general, curing and separating discrete portions of a given layer of the resin substantially continuously can reduce fabrication time.

In some implementations, the media source 706 can include a dispersion section 719, a collection section 721, and a reservoir 723 in fluid communication with the dispersion section 719 and the collection section 721. The dispersion section 719 can be along a first side of the transparent portion 715 of the media source 706, and the collection section 721 can be along a second side, different from the first side, of the transparent portion 715 of the media source 706. The first side and the second side can be, for example, opposite one another. In use, resin can be drawn from the reservoir 723 to the dispersion section 719 (e.g., through the use of one or more rollers in the reservoir 723). The dispersion section 719 can include, in some instances, a nozzle (e.g., shaped as a slit) and, further or instead, can be heated to facilitate flowing the resin through the dispersion section 719 to the transparent portion 715 of the media source 706.

In certain instances, the media source 706 can include a blade 725 movable to spread resin from the dispersion section 719 across the transparent portion 715 of the media source 706. For example, the blade 725 can pivot about a point to spread the resin across the transparent portion 715 of the media source 706. Additionally, or alternatively, the blade 725 can be movable to move at least a portion of the resin, such as excess resin from a previous layer, to the collection section 721. The resin moved to the collection section 721 can be agitated and/or heated to decrease the likelihood that particles in the resin will settle in the reservoir 723.

Figure 8:
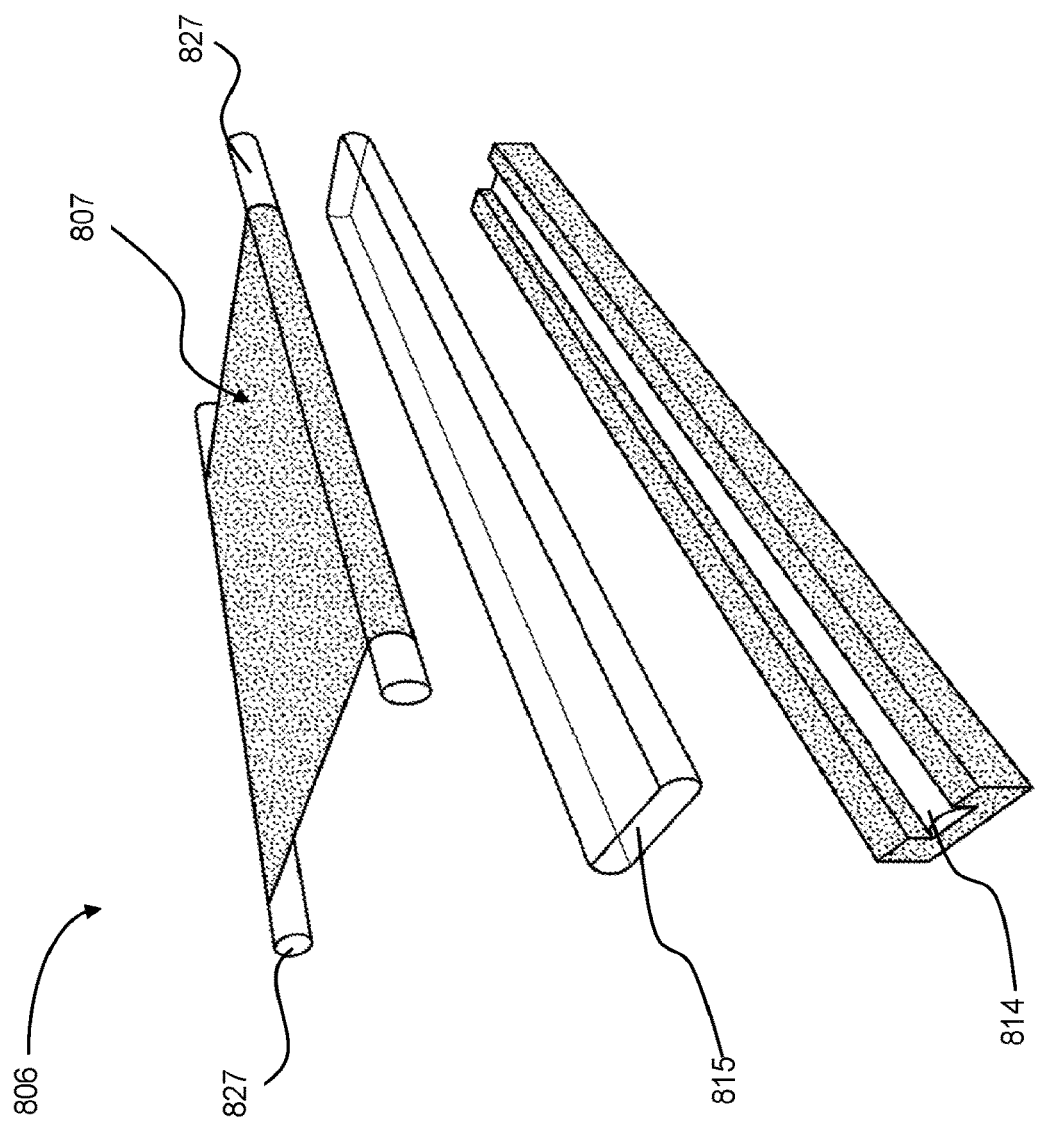
FIG. 8 is an exploded view of a portion of a media source of a fabrication system.

While a media source has been described as including a dispensing section and a collection section on either side of a transparent portion of the media source, other configurations for distributing a resin over a transparent portion of the media source are additionally or alternatively possible. For example, referring now to FIG. 8, a media source 806 can include a film 807, an activation light source 814, and a transparent portion 815. Unless otherwise specified or made clear from the context, it should be understood that the media source in FIG. 8 can be used in the fabrication system 700 of FIG. 7A-7B, in addition to or instead of the media source 706.

In the media source 806, a resin can be disposed on the film 807, and the film 807 can be movable across the transparent portion 815 of the media source 806. For example, the film 807 can be advanced over the transparent portion 815 of the media source 806 through movement of rollers 827 on other side of the transparent portion 815. In certain instances, the film 807 can be indexable by a predetermined width. As a specific example, the film 807 can be indexable by a width substantially equal to the width of the transparent portion 815 of the media source 806 such that, as the transparent portion 815 of the media source 806 is incremented in a direction parallel to a build surface (e.g., the surface 717 in FIG. 7A), the film 807 can be indexed with each incremental movement of the transparent portion 815 of the media source 806. It should be appreciated that, through such indexing of the film 807 with incremental movement of the transparent portion 815 of the media source 806, a fresh panel of resin will be disposed over the transparent portion 815 of the media source 806 at each increment, before activation light is directed at the resin to cure a discrete portion of a layer of the resin. The film 807 can be formed of any one or more of the materials described above with respect to the film 502 in FIG. 5. More generally, the film 807 can be understood to be analogous to the film 502 in FIG. 5, unless otherwise specified or made clear from the context.

Figure 9:
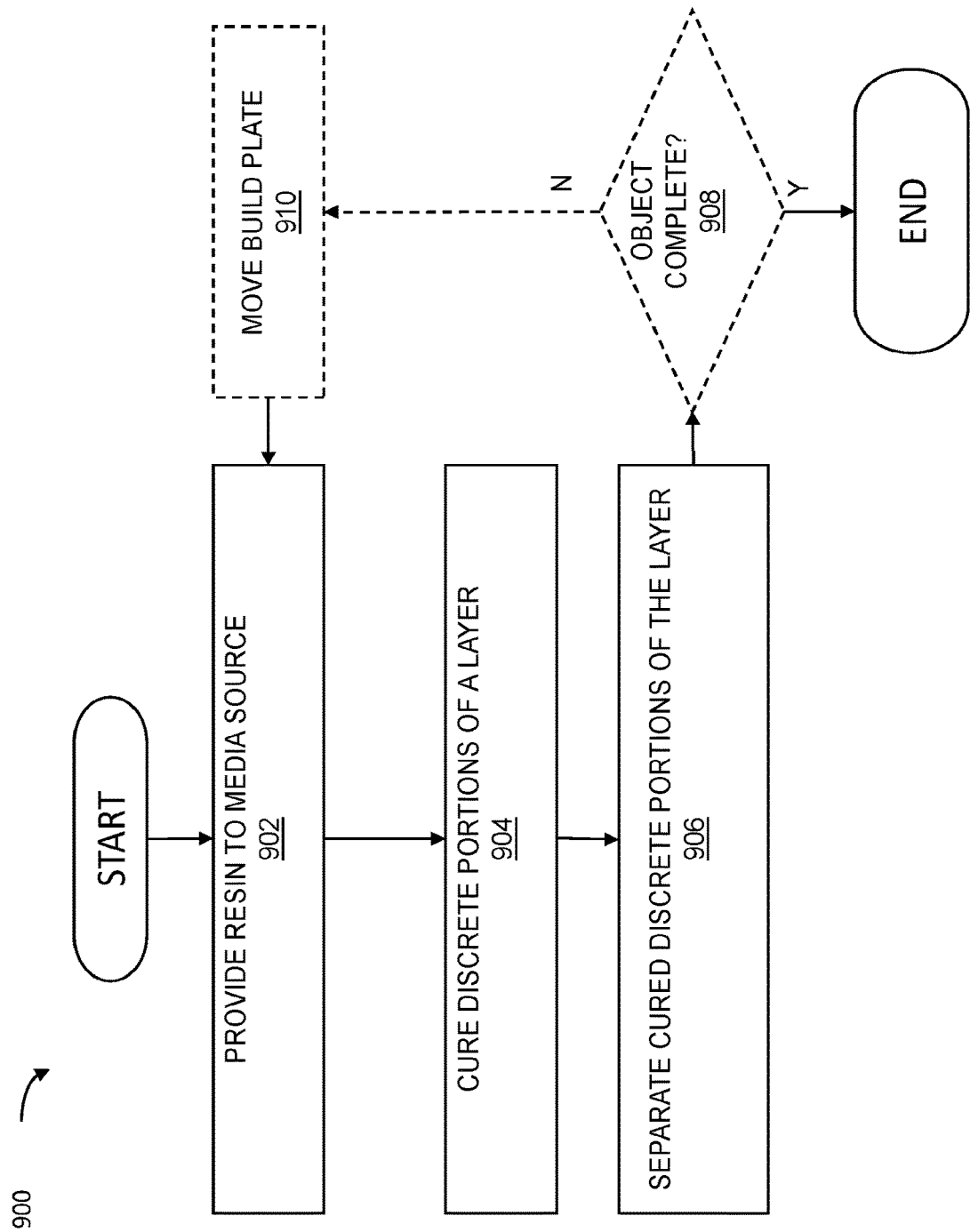
FIG. 9 is a flow chart of an exemplary method of fabricating a three-dimensional object through stereolithography.

FIG. 9 is a flowchart of an exemplary method 900 of fabricating a three-dimensional object. Unless otherwise specified or made clear from the context, the exemplary method 900 can be implemented using any one or more of the various different stereolithography systems described herein. For example, the exemplary method 900 can be implemented as computer-readable instructions stored on the computer readable storage medium 122 (FIG. 1) and executable by the controller 120 (FIG. 1) to operate the stereolithography system 100 (FIG. 1) including one or more of the fabrication systems of FIGS. 7A, 7B, and 8.

As shown in step 902, the exemplary method 900 can include providing resin to a media source disposed within a working volume defined by a build chamber. The resin can be any one or more of the resins described herein, unless otherwise specified or made clear from the context. More generally, the resin can include one or more binders and particles (e.g., metal particles) suspended in the one or more binders. At least one of the one or more binders can be curable (e.g., crosslinkable or polymerizable) upon exposure to energy, such as light of a sufficient wavelength. As an example, providing the resin to the media source can include moving the resin from a reservoir as described with respect to FIGS. 7A and 7B. Additionally, or alternatively, providing the resin to the media source can include moving the resin as described with respect to FIG. 8.

As shown in step 904, the exemplary method 900 can include curing discrete portions of a layer of the resin on a substrate carried on a surface of a build plate in the working volume. Curing the discrete portions of the layer can include directing light energy into the working volume through a transparent portion of the media source according to any one or more of the methods described herein. Accordingly, curing discrete portions of the layer of the resin can include curing the layer of the resin in multiple curing steps according to any one or more of the discrete curing methods described herein. Thus, for example, during discrete portions of the layer of the resin can include substantially continuously curing adjacent discrete portions of the layer of the resin and, in concert with such curing, shearing the cured resin in the discrete portions as part of a substantially continuous process. In certain instances, each discrete portion can span a dimension of the surface of the build plate. In such instances, light energy can be selectively delivered to a layer of resin by moving the transparent portion of the media chamber in a single direction (e.g., transverse to the spanned dimension). Thus, for example, the transparent portion of the media source and the activation light source can be arranged as a substantially elongate light bar (such as the activation light source 714) that can scan the layer of resin by moving in a single direction substantially parallel to the surface of the build plate.

As shown in step 906, the exemplary method 900 can include separating the cured discrete portions of the layer from the media source. The separation of at least one of the cured discrete portions can be done independently of separation of at least another one of the cured discrete portions. For example, at least one of the cured discrete portions of the layer can be separated from the media source before another one of the cured discrete portions of the layer is formed. As a more specific example, the step 904 of curing and the step 906 of separating can be performed alternately as the position of the media source is changed relative to the surface of the build plate. In sufficiently rapid succession, alternation of the step 904 of curing and the step 906 of separating can form the basis of a substantially continuous process applied across a given layer.

In general, separation of the cured discrete portions of the layer from the media source can include changing a position of the transparent portion of the media source relative to the build plate (e.g., the surface of the build plate). The changed position can generate a force (e.g., a shear force) on one or more of the cured discrete portions of the layer to separate each corresponding cured discrete portion from the media source.

In certain instances, one or both of the build plate and the transparent portion of the media source can be movable relative to one another to generate the force on the one or more cured discrete portions of the layer. For example, separating the cured portions of the layer from the media source can include moving one or both of the build plate and the transparent portion of the media source in a direction having a component parallel to the layer of the resin. Additionally, or alternatively, separating the cured discrete portions of the layer from the media source can include rotating one or both of the build plate and the transparent portion of the media source relative to one another. As one example, one or both of the surface of the build plate and the transparent portion of the media source can be rotated about an axis substantially perpendicular to a plane defined by the transparent portion of the media source.

As shown in step 908, the exemplary method 900 can include, for a plurality of layers, repeating the steps of providing resin to the media source, curing discrete portions of a given layer, and separating cured discrete portions of the layer can be repeated to form each layer of a three-dimensional object.

As shown in step 910, the exemplary method 900 can, optionally, include moving the build plate (e.g., in a direction away from the media source) before repeating the steps of providing resin to the media source, curing discrete portions of a given layer, and separating cured discrete portions of a given layer. Moving the build plate in this way can provide spacing necessary for forming a subsequent layer of the three-dimensional object.

Figure 10:
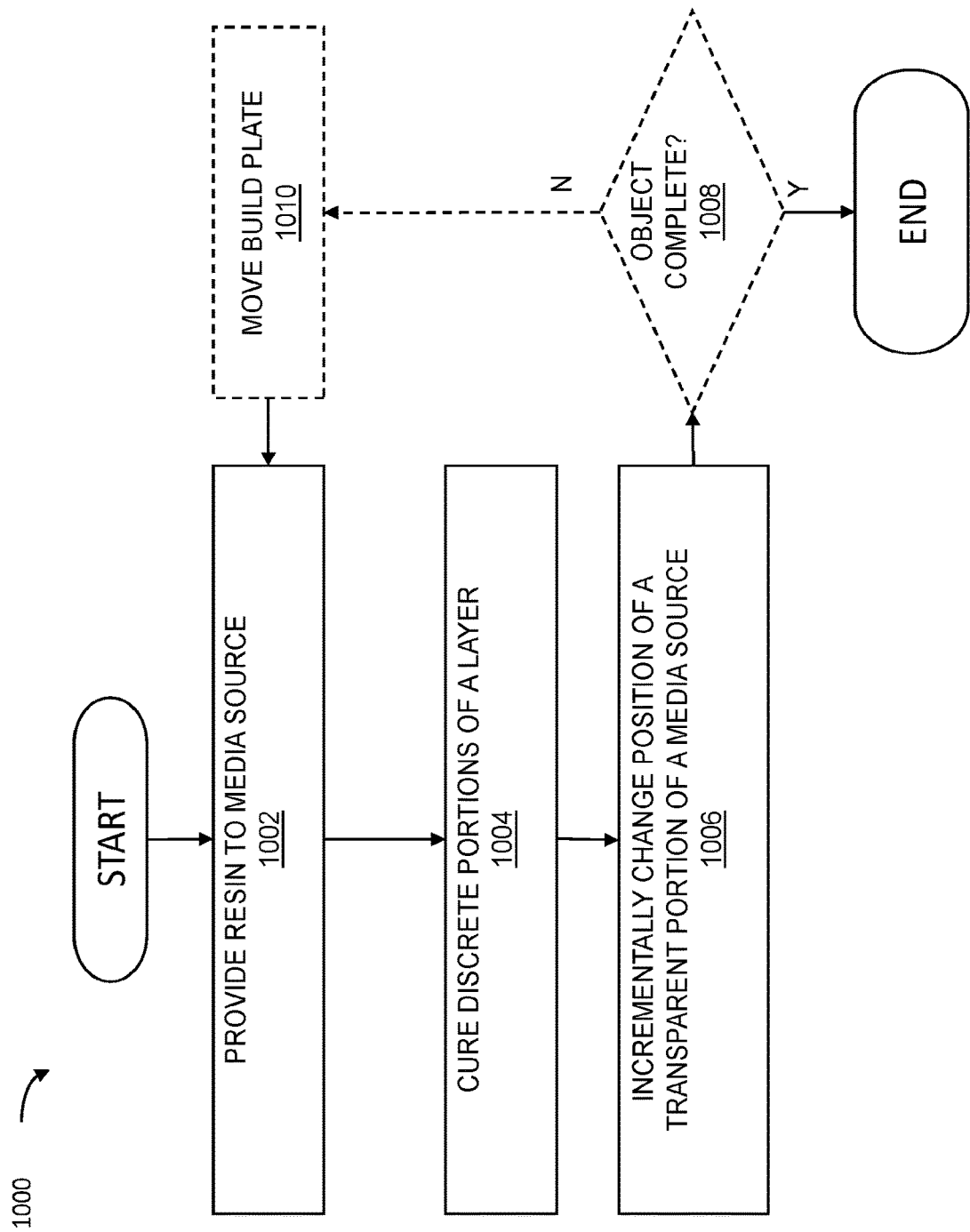
FIG. 10 is a flow chart of an exemplary method of fabricating a three-dimensional object through stereolithography.

FIG. 10 is a flow chart of an exemplary method 1000 of fabricating a three-dimensional object. Unless otherwise specified or made clear from the context, the exemplary method 1000 can be implemented using any one or more of the various different stereolithography systems described herein. For example, the exemplary method 1000 can be implemented as computer-readable instructions stored on the computer readable storage medium 122 (FIG. 1) and executable by the controller 120 (FIG. 1) to operate the stereolithography system 100 (FIG. 1) including one or more of the fabrication systems of FIGS. 7A, 7B, and 8.

As shown in step 1002, the exemplary method 1000 can include providing a resin to a media source disposed within a working volume defined by a build chamber. The resin can be, for example, any one or more of the resins described herein, and the media source can be any one or more of the media sources of the fabrication systems of FIGS. 7A, 7B, and 8.

As shown in step 1004, the exemplary method 1000 can include curing discrete portions of a layer of the resin on a substrate carried by a build plate in the working volume. In general, curing discrete portions of the layer of the resin on the substrate can include any one or more of the methods of curing discrete portions of the layer described herein. For example, the selective exposure of each discrete segment can be based on a predetermined pattern associated with the given segment of the layer. It should be appreciated that the predetermined patterns of each segment combine to form an overall predetermined pattern of the given layer.

As shown in step 1006, the exemplary method 1000 can include changing the position of the transparent portion of the media source relative to the build plate by an increment substantially equal to a width of the transparent portion of the media source. The change in position of the transparent portion of the media source can separate at least one of the cured discrete portions from the media source. In general, changing the position of the transparent portion of the media source relative to the build plate can include any one or more methods of changing the relative position of the media source relative to the build plate described herein. Thus, for example, changing the position of the transparent portion of the media source relative to the build plate can include moving one or both of the build plate and the media source relative to one another (e.g., to create a shear force in one or more cured discrete portions of the layer of resin). Further, or instead, the transparent portion of the media source can be moved in increments of one width (e.g., with each increment substantially adjacent to a previous position of the transparent portion) in a direction substantially parallel to the surface of the build plate as the discrete portions of the layer of the resin are cured for a given layer of a three-dimensional object.

As shown in step 1008, the exemplary method 1000 can include, for each layer of a plurality of layers, repeating the steps of providing resin to the media source, curing discrete portions of a given layer, and separating cured discrete portions of the given layer can be repeated to a three-dimensional object.

As shown in step 1010, the exemplary method 1000 can include moving the build plate (e.g., in a direction away from the media source) before repeating the steps of providing resin to the media source, curing discrete portions of a given layer, and separating cured discrete portions of a given layer.

While certain fabrication systems have been described for delivering resin to discrete planar portions of a layer and curing each discrete planar portion of the given layer, other configurations are additionally or alternatively possible. For example, referring now to FIG. 11, a fabrication system 1100 can be based on delivering resin and curing resin along a region of tangential contact between a rolling member and a substrate upon which a given layer is being formed. The fabrication system 1100 can include media source 1102, a build plate 1104, and an activation light source 1106. Unless otherwise specified or made clear from the context, the fabrication system 1100 can be part of any one or more of the stereolithography systems described herein. Thus, for example, it should be understood that the fabrication system 1100 can be part of the stereolithography system 100 (FIG. 1) and, therefore, the media source 1102 and the build plate 1104 of the fabrication system 1100 can be disposed in the working volume 112 defined by the build chamber 110.

The activation light source 1106 can be positioned to direct activation light, through the media source 1102, toward a surface of the build plate 1104. The activation light source 1106 can be, for example, any of the various different light sources described herein. Light energy moving from the activation light source 1106 can pass through a transparent portion 1110 of the media source 1102 and, in some instances, can remain substantially unchanged.

The media source 1102 can be rotatable about an axis substantially parallel to the surface of the build plate 1104 in a direction R to create a shear force to separate one or more cured discrete portions of a layer of a resin 1114 from the media source 1102. Thus, for example, as a discrete portion of the layer of the resin 1114 is cured, the media source 1102 can be rotated (e.g., by a predetermined amount) to separate the cured discrete portion from the media source 1102. In addition to the rotational motion of the media source 1102 in the direction R, one or both of the media source 1102 can and the build plate 1104 can be movable relative to the other one of the media source 1102 and the build plate 1104 in a direction D substantially parallel to a surface 1108 of the build plate 1104. In general, the components of rotational and translational relative movement between the media source 1102 and the surface 1108 of the build plate 1104 can be controlled to achieve a direction and speed of movement useful for curing and separating discrete segments of the resin 1114 to form a given layer of a three-dimensional object. Further or instead, the build plate 1104 can be movable in a direction perpendicular to the surface 1108 of the build plate 1104. For example, the build plate 1104 can move in the direction perpendicular to the surface 1108 of the build plate 1104 following formation of a given layer (e.g., to make space for a new layer to be built upon the given layer).

In certain implementations, the media source 1102 can include a substantially cylindrical tube transparent to light from the activation light source 1106. For example, the substantially cylindrical tube can have a longitudinal dimensional substantially parallel to the surface of the build plate, and the substantially cylindrical tube can be rotatable about the longitudinal dimension to move the media source 1102 relative to the substrate upon which a given layer is being formed. The longitudinal dimension of the substantially cylindrical tube can span a dimension of the surface of the build plate 1104.

In some implementations, the media source 1102 can be disposed about the activation light source 1106. Such a position of the media source 1102 about the activation light source 1106 can facilitate, for example, isolating (e.g., thermally isolating) the activation light source 1106 from other components of the fabrication system 1100. For example, in instances in which the media source 1102 is a substantially cylindrical tube, the activation light source 1106 can be disposed in an interior portion of the tube, where the activation light source 1106 can be protected from heat and debris, among other things.

In some instances, the fabrication system 1100 can further include a reservoir 1112. The media source 1102 can be, for example, partially disposed in the reservoir 1112, with rotation of the media source 1102 moving a surface of the media source 1102 in the direction R from the reservoir 1112 toward the surface 1108 of the build plate 1104. Continuing with this example, as the media source 1102 rotates in the direction R from the reservoir 1112 toward the surface 1108 of the build plate 1104, the media source 1102 can deliver the resin 1114 to a position between the activation light source 1106 and the surface 1108 of the build plate 1104, where light energy from the activation light source 1106 can cure a discrete portion of a layer of the resin. In addition to delivering resin toward the build plate 1104, rotation of the media source 1102 in the direction R can return unused resin 1114' to the reservoir 1112.

The reservoir 1112 can include, for example, at least one mixer 1116 disposed in the reservoir 1112. The at least one mixer 1116 can include a plurality of blades 1118 rotatable or otherwise movable in the reservoir 1112 to agitate the resin in the reservoir 1112. Such agitation can, for example, reduce the likelihood that particles in the resin will settle in the reservoir 1112. Further, or instead, the fabrication system 1100 can include a heater 1120 in thermal communication with the reservoir 1112. In certain instances, heat from the heater 1120 can facilitate mixing of the resin 1114 by the at least one mixer 1116.

Figure 11:
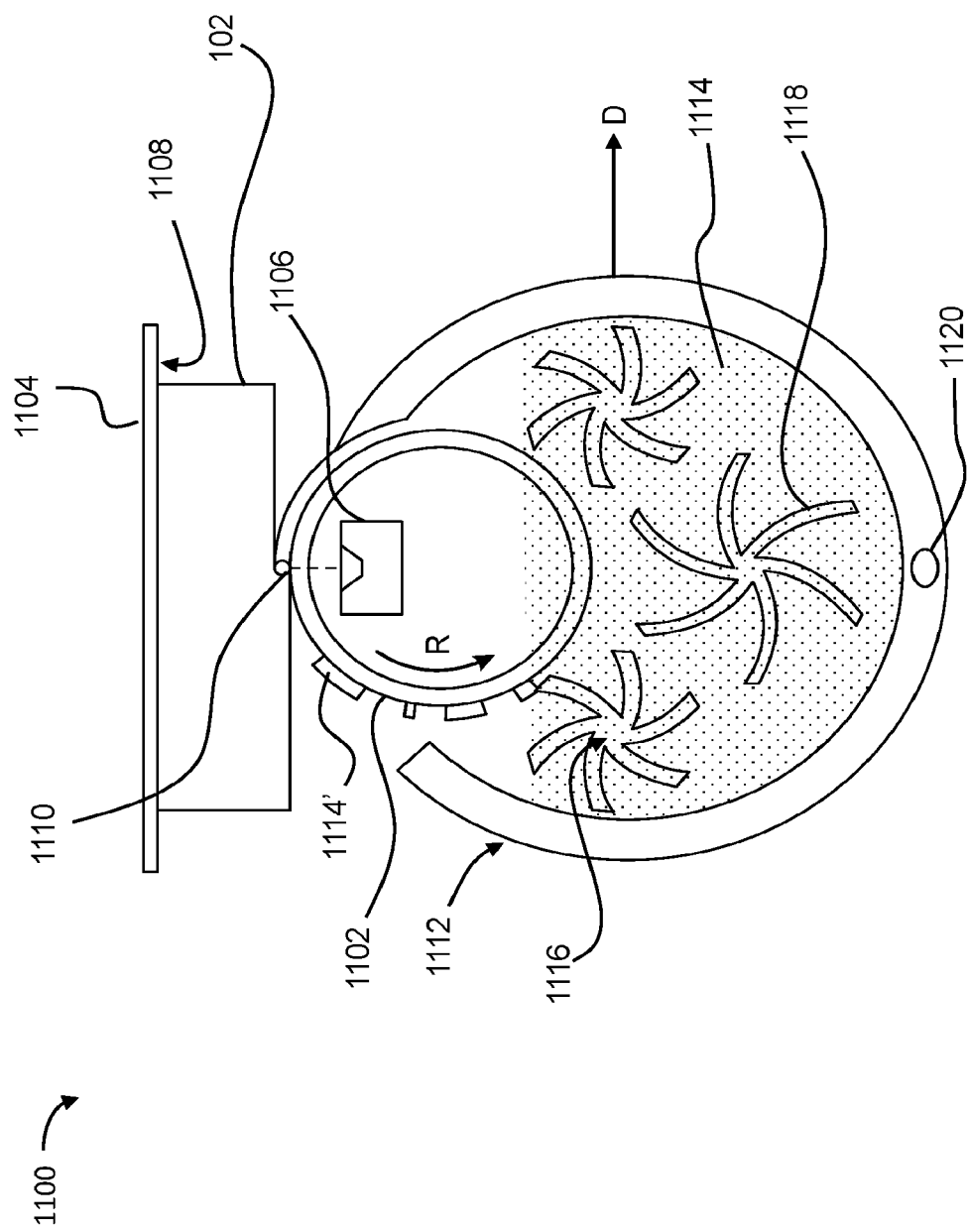
FIG. 11 is a schematic representation of a fabrication system of a stereolithography system.
Figure 12:
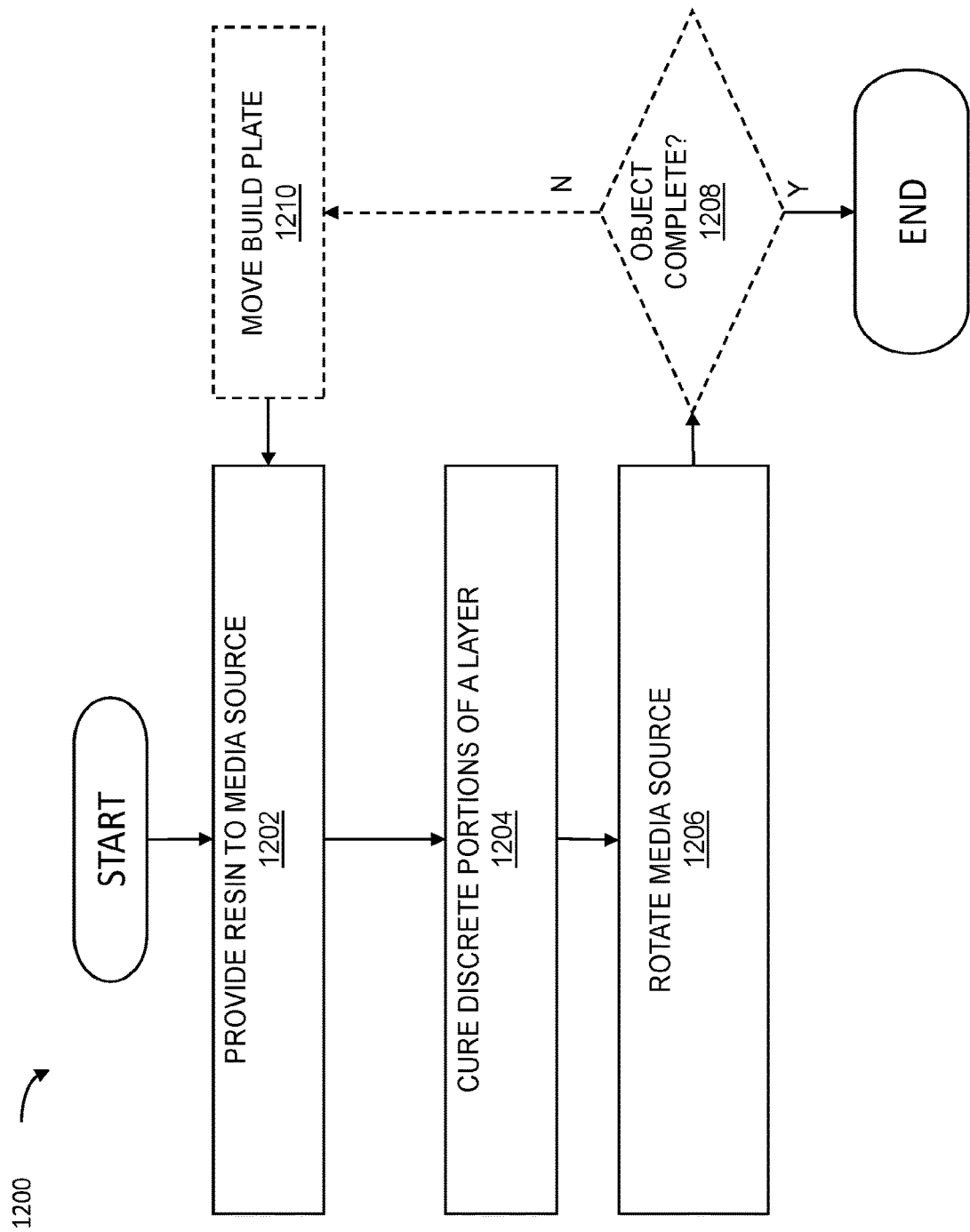
FIG. 12 is a flow chart of an exemplary method of fabricating a three-dimensional object through stereolithography.

FIG. 12 is a flow chart of an exemplary method 1200 of fabricating a three-dimensional object using a rotatable media source. By way of example, the exemplary method 1200 can be implemented as computer-readable instructions stored on the computer-readable storage medium 122 (FIG. 1) and executable by the controller 120 (FIG. 1) to operate the stereolithography system 100 (FIG. 1) including the fabrication system 1100 (FIG. 11).

As shown in step 1202, the exemplary method 1200 can include providing a resin to a media source disposed within a working volume defined by a build chamber. The resin can be, for example, any one or more of the resins described herein. Providing the resin to the media source can include, for example, storing the resin in a reservoir with at least a portion of the media source in contact with the resin in the reservoir.

As shown in step 1204, the exemplary method 1200 can include curing discrete portions of a layer of the resin on a substrate carried on a surface of a build plate in the working volume. For example, curing discrete portions of the layer of the resin on the substrate can include directing light energy through the media source and at the discrete portions of the layer on the substrate. In certain instances, directing light energy at the discrete portions of the layer on the substrate can include pausing rotation of the media source as light energy is directed at each discrete portion of the layer.

As shown in step 1206, the exemplary method 1200 can include rotating the media source about an axis substantially parallel to the surface of the build plate. The rotation of the media source can, for example, separate at least one of the cured discrete portions from the media source. As the media source is rotated about the axis substantially parallel to the surface of the build plate, at least a portion of the media source can move through the reservoir containing the resin. In particular, the media source can move through the resin such that resin can be deposited on the media source and rotation of the media source draws resin out of the reservoir to a position between the activation light source and the surface of the build plate. The resin in the reservoir can be mixed, heated, or both according to any one or more of the methods described herein.

Other types of movement of the media source relative to the surface of the surface of the build plate are additionally, or alternatively, possible. For example, one or both of the build plate and the media source can be moved relative to one another to change a position of the media source relative to the surface of the build plate in a direction substantially parallel to the surface of the build plate.

As shown in step 1208, the exemplary method 1200 can include, for each layer of a plurality of layers, repeating the steps of providing the resin to the media source, curing discrete portions of each given layer, and separating cured discrete portions of the each given layer to form a three-dimensional object.

In some instances, as shown in step 1210, the exemplary method 1200 can include moving the build plate (e.g., in a direction away from the media source) before building a subsequent layer of the three-dimensional object being formed.

While resins have been described as including particles suspended in one or more binders, other configurations are additionally or alternatively possible. For example, as described in greater detail below, resins can include particles that are substantially transparent to light of certain wavelengths. In general, substantial transparency of particles in a resin can facilitate achieving suitable penetration of light through a layer of the resin and, in turn, can be useful for forming bonds between a layer being formed and an immediately preceding layer to form a three-dimensional object. Stated differently, substantial transparency of the particles in the resin can usefully overcome disparate challenges associated with achieving suitable light penetration in a layer of a resin to achieve sufficient intralayer bonding while the resin itself includes a high particle loading useful for forming a dense part.

Figure 13:
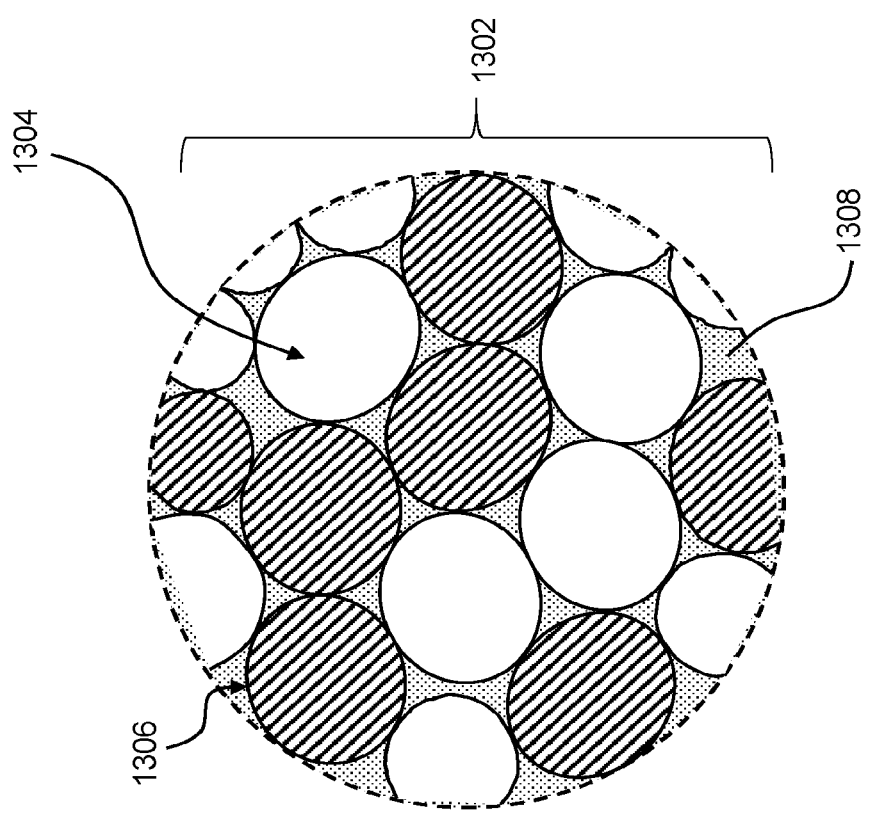
FIG. 13 is a schematic representation of a cross-section of a resin including particles of a first material, particles of a second material, and a binder system.

Referring now to FIG. 13, a resin 1302 can include particles of a first material 1304, particles of a second material 1306, and a binder system 1308 in which the particles of the first material 1304 and the particles of the second material 1306 are suspended (e.g. substantially homogeneously suspended). The particles of the second material 1306 can be different from the particles of the first material 1304. For example, particles of the first material 1304 can be substantially transparent to light of a wavelength sufficient to crosslink, polymerize, or both at least one portion of the binder system (e.g., light having a wavelength of about 300 nm to about 450 nm). Additionally, or alternatively, the particles of the second material 1306 can include a metal or a material otherwise substantially opaque to light of the wavelength sufficient to crosslink, polymerize, or both, the at least one portion of the binder system 1308. Thus, it should be appreciated that, in a resin having a high loading of particles, the substantial transparency of the particles of the first material 1304 to light of the wavelength sufficient to crosslink and/or polymerize at least one portion of the binder system 1308 can provide a pathway for the penetration of light to a suitable depth within a layer of a three-dimensional object being formed.

In certain instances, the particles of the second material 1306 can have an average size less than the wavelength of the light sufficient to crosslink, polymerize, or both, the at least one portion of the binder system 1308. Thus, in implementations, in which the particles of the second material 1306 are substantially opaque, the particles of the second material 1306 can be sized to be less likely to interfere with penetration of light into the resin 1302.

The particles of the first material 1304 can include, for example, a ceramic. In some implementations, the ceramic can be heated or otherwise chemically converted to form a metal suitable for formation of the three-dimensional object. In certain instances, at least one portion of the binder system 1308 can be crosslinkable, polymerizable, or both, through exposure to light of a wavelength below a band gap of the ceramic. As an example, the ceramic can include a metal oxide, such as any one or more of iron oxide, silicon oxide, aluminum oxide, zirconium oxide, and chromium oxide. Additionally, or alternatively, the ceramic can include a metal nitride, such as any one or more respective metals selected from group VII or group VIII elements. Further or instead, the ceramic can include a metal carbide (e.g., silicon carbide).

In certain instances, the particles of the first material 1304 can include one or more of an intermetallic and a ternary oxide.

The particles of the first material 1304 can be, in certain applications, chemically convertible to a third material. Thus, for example, an appropriate first material for certain applications can include selecting a material that is optically transparent to a wavelength suitable for cross-linking and/or polymerizing at least a portion of a binder system 1308 while also being chemically convertible (e.g., through subsequent processing) to a third material useful for fabrication of the three-dimensional object. As a specific example, the first material can be selected such that the third material is substantially the same composition as the second material. As a more specific example, the second material can include copper, and the first material can be copper sulfide. Additionally, or alternatively, the first material can be selected for being chemically convertible to a given third material through a desired process, such as a typical post-process performed on the three-dimensional object formed through layer-by-layer deposition of the resin 1302 according to any one or more of the stereolithography methods described herein. By way of example, the first material can be selected as being chemically convertible to the third material via thermally-activated decomposition or reduction. Thus, in the case in which the third material is substantially the same composition as the second material, the first material can be selected as being chemically convertible to the second material via thermally-activated decomposition or reduction. Further, or instead, the first material can be a metal oxide reduceable to form a metal. As described in greater detail below, the first material can be a material that is chemically convertible to a material that can be alloyed with the second material in instances in which the second material includes a metal.

The volumetric ratio of the particles of the first material 1304 to the particles of the second material 1306 can be a function of considerations related to achieving suitable penetration of light while also producing an acceptable amount of shrinkage in a three-dimensional object as the first material is converted to the third material. For example, the particles of the second material 1306 can be greater than about 10 percent by volume and less than about 30 percent by volume of the resin 1302. Additionally, or alternatively, the particles of the first material 1304 can be greater than about 20 percent and less than about 40 percent by volume of the resin 1302.

The binder system 1308 can include a first binder and a second binder. The first binder and the second binder can include combinations of any one or more of the first binder and the second binder described herein. Thus, as an example, the first binder can be substantially non-reactive under exposure to the wavelength of light sufficient to crosslink or polymerize the second binder and, additionally or alternatively, the first binder can be useful for facilitating spreading the resin 1302 as part of a fabrication process.

Figure 14:
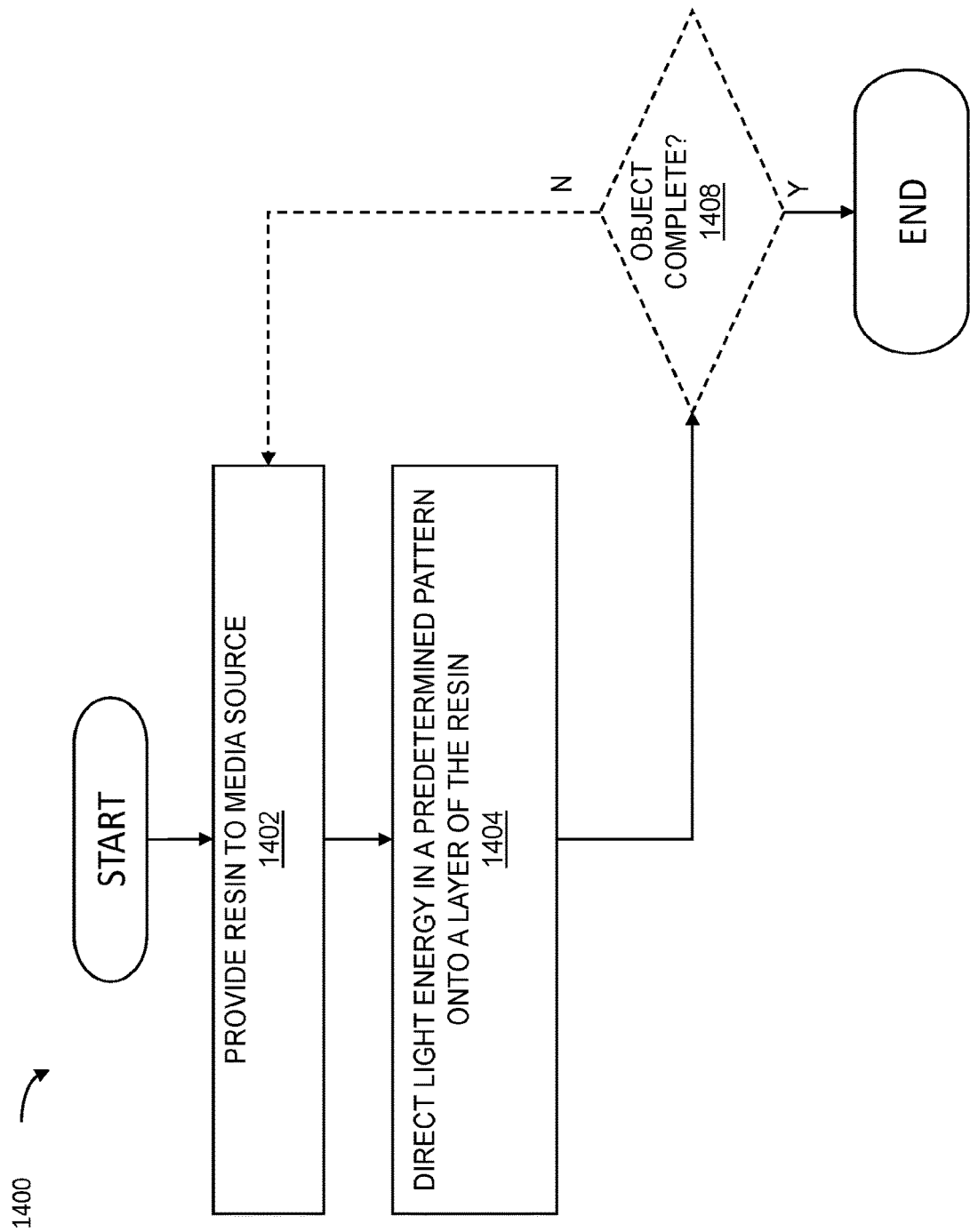
FIG. 14 is a flow chart of an exemplary method of additive manufacturing of a three-dimensional object using a resin including particles substantially transparent to light energy.

FIG. 14 is a flow chart of an exemplary method 1400 of additive manufacturing of a three-dimensional object using a resin including particles substantially transparent to light energy and suspended in a binder system. Unless otherwise indicated or made clear from the context, it should be appreciated that the exemplary method 1400 can be carried out using any one or more of the devices and systems of the present disclosure.

As shown in step 1402, the exemplary method 1400 can include providing a resin to a media source. The resin can include particles of a first material, particles of a second material, and a binder system in which the particles of the first material and the second material are suspended and, thus, more specifically, can be the resin 1300 in FIG. 13.

As shown in step 1404, the exemplary method 1400 can include directing light energy in a predetermined pattern onto a layer of the resin on the media source. The light energy can modify the resin, such as by cross-linking, polymerizing, or both, at least one portion of the binder system. Further, or instead, the particles of the first material can be substantially transparent to the light energy, and the light energy can substantially penetrate the layer (e.g., penetrate the entire thickness of the layer) to bind a given layer of the resin to an adjacent layer as part of a fabrication process of the three-dimensional object.

As shown in step 1408, the exemplary method 1400 can include, for each layer of a plurality of layers, repeating the steps of providing resin to the media source, and directing light energy in a predetermined pattern onto a given layer of the resin on the media source to form a three-dimensional object.

While resins have been described as including particles of a first material and particles of a second material to facilitate penetration of light into a layer formed by the resin, it should be appreciated that the first material and the second material can additionally, or alternatively, be selected to form a desired alloy in the finished three-dimensional object.

Referring again to FIG. 13, the particles of the first material 1304 can include, for example, one or more of a ceramic, an intermetallic, or other material substantially transparent to light of a wavelength sufficient to crosslink, polymerize, or both, at least one portion of the binder system 1308. The particles of the first material 1304 can be chemically convertible to a first metal (e.g., via reduction of a metal oxide), and the particles of the second material 1306 can include a second metal alloyable with the first metal. Thus, in use, the particles of the first material 1304 can be penetrated by light to bind a given layer to an adjacent layer and, once a three-dimensional object is formed through a layer-by-layer stereolithography process, the particles of the first material 1304 can be converted into a material alloyable with the second metal. Further, while a first metal and a second metal are described, it should be appreciated that additional metals and/or additives can be included in the resin as necessary to achieve a target alloy formulation in a finished part. In certain instances, the particles of the first material 1304 can be in a relative concentration to the particles of the second material 1306 such that an alloy including the first metal and the second metal meets a predetermined material standard. For example, the alloy including the first metal and the second metal can meet an AISI material standard or other similar industry standard.

In certain implementations, the first metal and the second metal can be alloyable into a stainless steel. For example, the first material can be an iron-based ceramic and the second material can be one or more of chromium nickel, or alloys thereof. Examples of the iron-based ceramic include one or more of iron oxide and iron nitride.

The selection of an appropriate first material and an appropriate second material can be based on chemical stability. That is, because the first material undergoes chemical conversion to alloy with the second material, it is generally desirable to select the first material as the material that is more readily converted. Thus, for example, an oxide of the first metal can be less chemically stable than oxide of the second metal.

In certain implementations, particles of the first material can include a ternary oxide.

Figure 15:
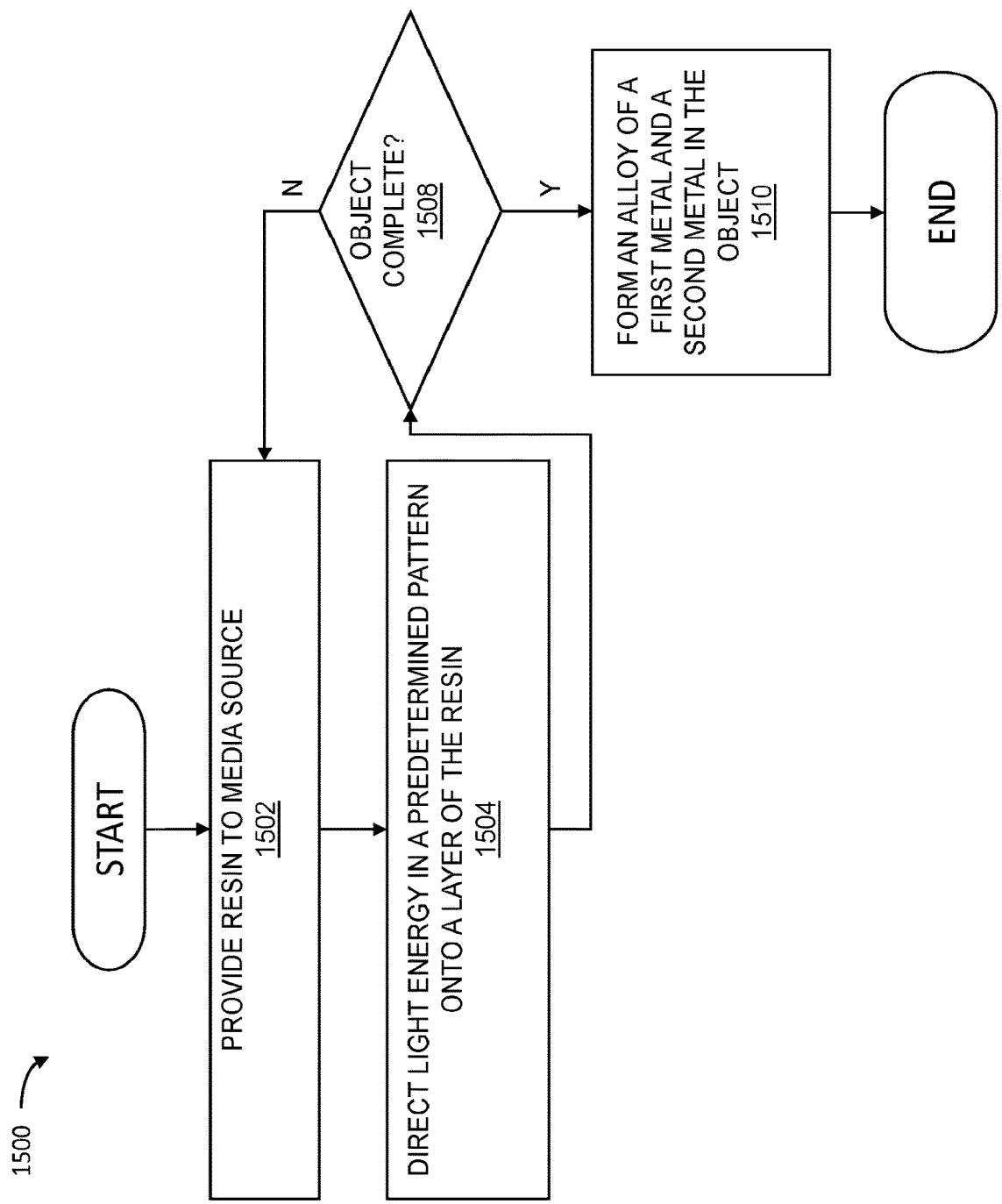
FIG. 15 is a flow chart of an exemplary method of additive manufacturing of a three-dimensional object by forming an alloy from particles suspended in a resin.

FIG. 15 is a flow chart of an exemplary method of additive manufacturing of a three-dimensional object by forming an alloy from particles suspended in a resin. Unless otherwise indicated or made clear from the context, it should be appreciated that the exemplary method 1500 can be carried out using any one or more of the devices and systems of the present disclosure.

As shown in step 1502, the exemplary method 1500 can include providing a layer of a resin on a media source. The resin can be any one or more of the resins described herein and including particles of a first material, particles of a second material, and a binder system and, more specifically, with the first material substantially transparent to light of a wavelength sufficient to cross-link or polymerize at least a portion of a binder system in which the particles are suspended, and the first material chemically convertible into a first metal alloyable with a second metal of the second material.

As shown in step 1504, the exemplary method 1500 can include directing light energy in a predetermined pattern onto the layer of the resin to cure the resin on a substrate carried by a build plate.

As shown in step 1508, the exemplary method 1500 can include, for each layer of a plurality of layers, repeating the steps of providing the resin, and directing light energy in a predetermined pattern onto a given layer of the resin. Unless otherwise indicated, or made clear from the context the steps 1504 and 1508 should be understood to be analogous to the corresponding steps 1404 and 1408 described with respect to the exemplary method 1400 (FIG. 14).

As shown in step 1510, the exemplary method 1500 can include forming an alloy including the first metal and the second metal. The alloy can be, for example, an alloy meeting a predetermined standard, such as one or more industry standards for a given type of alloy. As an alternative or additional example, the alloy can be a stainless steel.

Forming the alloy including the first metal and the second metal can include thermally processing the three-dimensional object. In certain implementations, the first material can be chemically converted to the first metal by sintering the three-dimensional object at a sintering temperature. Additionally, or alternatively, forming the alloy including the first metal and the second metal can include infiltrating (e.g., through wicking) the three-dimensional object with a liquid metal. The liquid metal can be, for example, a component of the alloy including the first metal and the second metal. Further, or instead, the liquid metal can include a third metal having a composition different from at least one of the first metal and the second metal.

In some instances, the exemplary method 1500 can, further or instead, include debinding the binder system from the three-dimensional object. By way of example, such debinding can include any one or more of the debinding processes described herein.

While the first material and the second material have been described as being metal or convertible into a metal, it should be appreciated that at least one of the first material and the second material can be an additive useful for forming an alloy. Further, or instead, it should be appreciated that the first material and the second material are recited for the sake of clarity of explanation and, more generally, the resin can include two or more materials processable (e.g., thermally processable) into an alloy.

While resins have been described as including particles of different compositions to facilitate formation of strong three-dimensional objects using stereolithographic processes, other resins are additionally or alternatively possible. For example, resins can include one or more photopolymers that can be usefully chemically converted to provide support for a three-dimensional object formed through a stereolithographic process as the three-dimensional object is thermally processed to densify and, ultimately, form a finished part.

As an example, a resin can include particles of metal (e.g., iron) and a binder system in which the particles are suspended. The binder system can include a photopolymer crosslinkable or polymerizable upon exposure to light of a predetermined wavelength. Additionally, or alternatively, the photopolymer can be thermally decomposable to a first ceramic dissolvable in the metal or an alloy of the metal at a sintering temperature of the particles of the metal. Thus, in this way, the ceramic can provide sintering support for strengthening the three-dimensional part without being present in significant quantities in the three-dimensional part after sintering.

The photopolymer can be, for example, a silicone polymer and the first ceramic can be silicon carbide. In certain implementations, the binder system can include a second component containing carbon. The second component can be chemically convertible such that the silicon carbide is formed from the carbon on of the second component.

In certain instances, the particles of the metal can have an average size less than the wavelength of the light sufficient to crosslink or polymerize the photopolymer. Such size can reduce the likelihood that the particles of the metal will interfere with penetration of the light in a layer of the resin.

The molecular weight of the photopolymer can be increasable from less than about 1000 g/mol to greater than about 1000 g/mol under exposure to the wavelength of light sufficient to crosslink or polymerize the photopolymer.

In general, the particles of metal suspended in the binder system can have a timescale of settling substantially greater than the duration of time sufficient for the photopolymer to undergo crosslinking or polymerization upon exposure to light of the predetermined wavelength.

Figure 16:
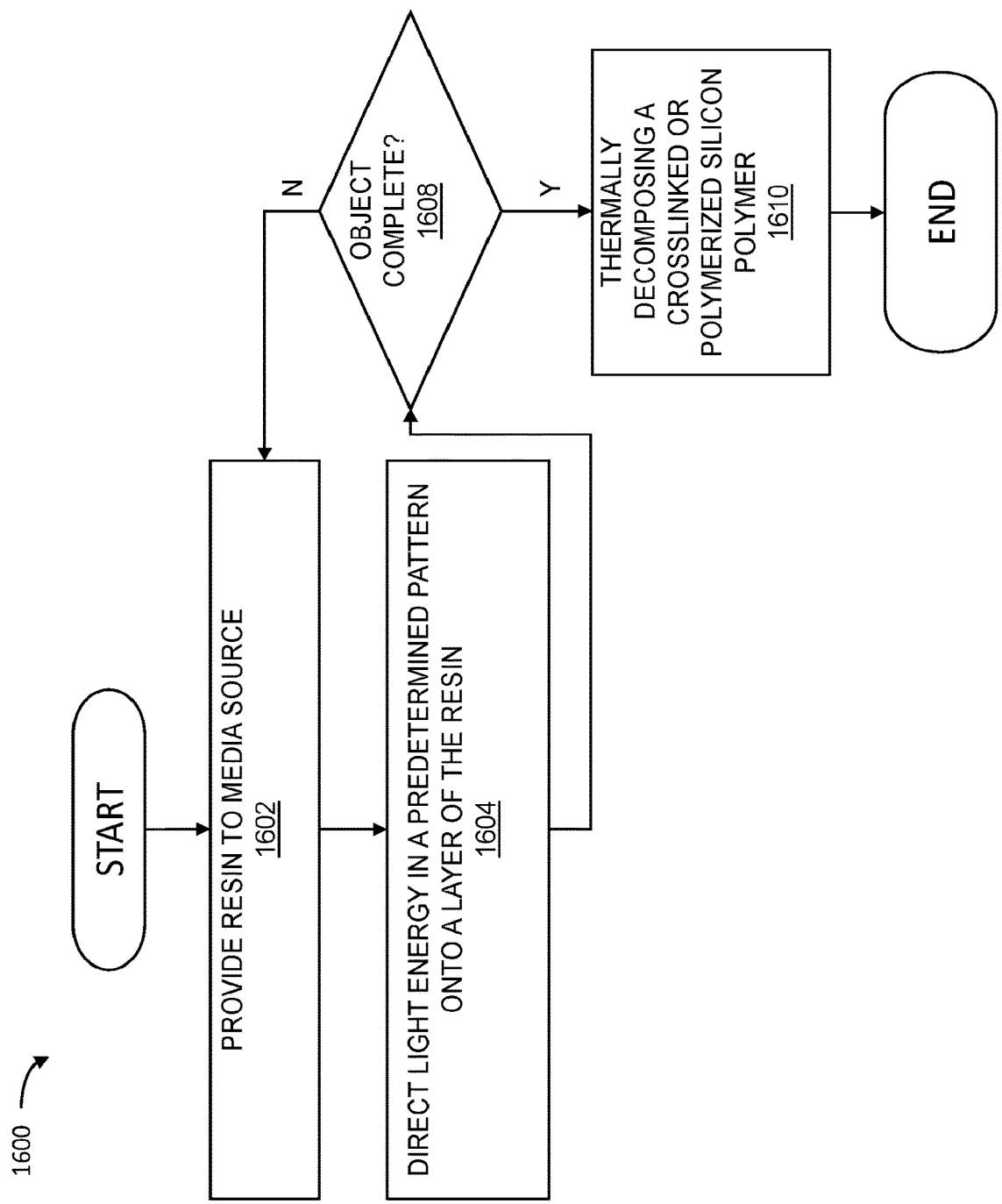
FIG. 16 is a flow chart of an exemplary method of additive manufacturing of a three-dimensional object using a resin including a silicone polymer.

FIG. 16 is a flow chart of an exemplary method 1600 of additive manufacturing of a three-dimensional object using a resin including a silicone polymer. Unless otherwise indicated or made clear from the context, it should be appreciated that the exemplary method 1600 can be carried out using any one or more of the devices and systems of the present disclosure.

As shown in step 1602, the exemplary method 1600 can include providing a resin to a media source. The resin can include a silicone polymer and, further or instead, particles of metal suspended in the silicone polymer. As shown in step 1604, the exemplary method 1600 can include directing light energy in a predetermined pattern in onto a layer of the resin on substrate carried by a build plate. The light energy can crosslink or polymerize the silicone polymer. Unless otherwise indicated or made clear from the context, it should be understood that steps 1602 and 1604 of the exemplary method 1600 are analogous to the corresponding steps 1402 and 1404 of the exemplary method 1400 (FIG. 14).

As shown in step 1608, the exemplary method 1600 can include, for each layer of a plurality of layers, repeating the steps of providing the resin and directing light energy in a predetermine pattern onto a given layer of a resin to form a three-dimensional object.

As shown in step 1610, the exemplary method 1600 can include thermally decomposing the crosslinked or polymerized silicone polymer into a ceramic. In implementations in which the resin includes particles of metal suspended in the silicone polymer, the exemplary method 1600 can include thermally processing (e.g., sintering) particles of metal in the three-dimensional object containing the ceramic. The ceramic can, for example, dissolve in the metal or an alloy of the metal as the particles of the metal are thermally processed. For example, the ceramic material can include silicon carbide and the alloy of the metal can include steel. Additionally, or alternatively, the exemplary method 1600 can include infiltrating a liquid metal into the ceramic material in the three-dimensional object. The ceramic material in the metal can be dissolved in the liquid metal or in an alloy of the metal of the liquid metal.

Figure 17:
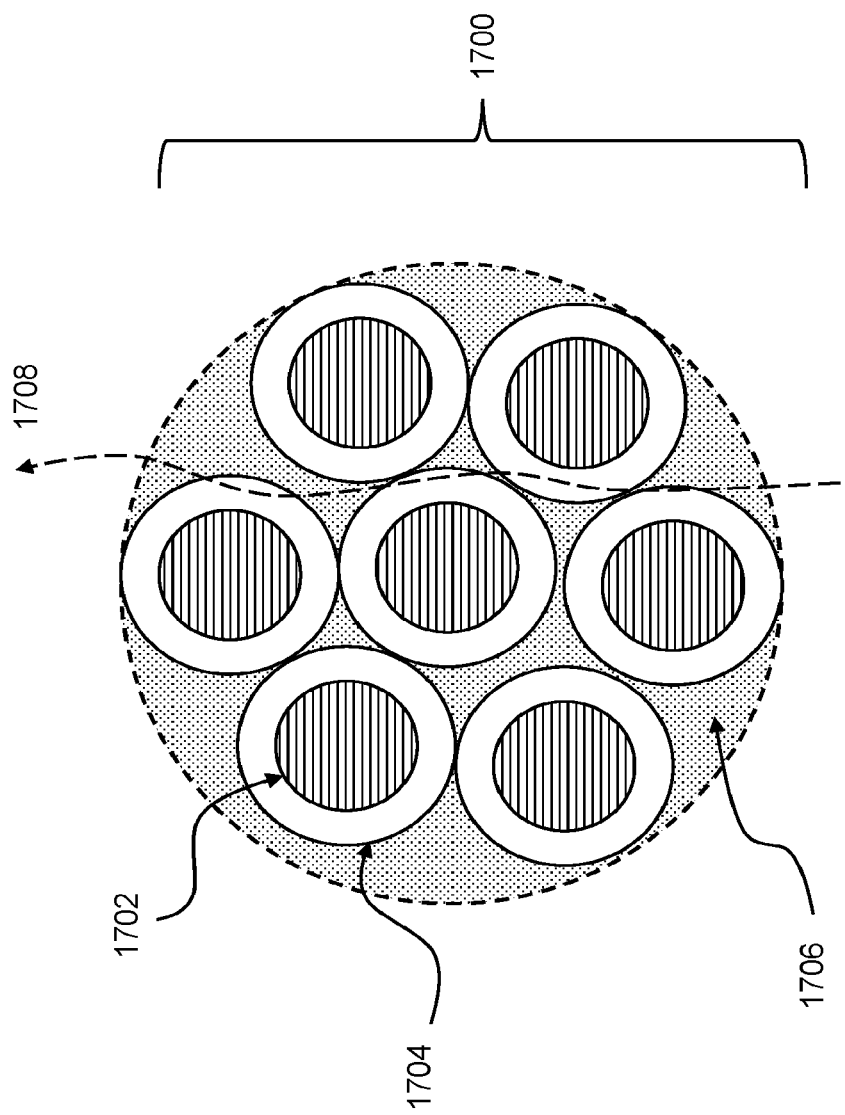
FIG. 17 is a schematic representation of a cross-section of a metal particle coated with a material.

While resins have been described as including particles of different materials to facilitate light penetration through a layer of the resin, other configurations are additionally or alternatively possible. For example, referring now to FIG. 17, a resin 1700 can include particles of a metal 1702 and a coating 1704 disposed on the particles of the metal 1702. The coating 1704 can be formed of a material different from the particles of the metal 1702, and the coating 1704 can have an average thickness of greater than about 3 percent and less than about 85 percent of an average diameter of the particles of the metal. It should be appreciated that a coating thickness in this range is substantially larger than natural oxide coatings that form on metals.

The particles of the metal 1702 and the coating 1704 can be suspended in a binder system 1706, which can include any one or more of the binders described herein. The material of the coating 1704 can be substantially transparent to light of a wavelength sufficient to crosslink, polymerize, or both, at least one portion of the binder system 1706 (e.g., a wavelength of about 300 nm to about 450 nm). Thus, it should be further understood that the coating 1704 can facilitate penetration of light through a layer of the resin including coated metal particles. An exemplary light path 1708 is shown passing through the resin 1700.

In general, the particles of the metal 1702 can be any of the various different metals described herein. Thus, for example, the particles of the metal 1702 can have an average size less than the wavelength of the light sufficient to crosslink, polymerize, or both, the at least one portion of the binder system 1706.

The material of the coating 1704 can include, for example, a ceramic. In such instances, the at least one portion of the binder system 1706 can be crosslinkable, polymerizable, or both, through exposure to light of a wavelength below a band gap of the ceramic. Further, or instead, the ceramic can include a metal oxide, which can include one or more of iron oxide, silicon oxide, aluminum oxide, zirconium oxide, and chromium oxide. Additionally, or alternatively, the ceramic can include a metal nitride, such as one or more nitrides of one or more respective metals selected from the group VII or group VIII elements. Still further in addition or further in the alternative, the ceramic can include a metal carbide (e.g., silicon carbide).

In general, the material of the coating 1704 can include any of the transparent materials described herein. Thus, for example, the material of the coating 1704 can include an intermetallic, a ternary oxide, or both. Further, or instead, the material of the coating 1704 can be chemically convertible to a metal (e.g., the metal of the particles). In certain implementations, the material of the coating 1704 can include a metal oxide, and the material of the coating 1704 can be chemically reducible to a metal (e.g., the metal of the particles or a component of an alloy).

While various different methods of providing a resin to a media source have been described, it should be appreciated the use of other thin coating techniques is additionally or alternatively possible. For example, known thin coating techniques such as one or more of slot die, tape casting, silk screen, and the like can be used to deposit thin layers of any one or more of the resins described herein onto a substrate as part of a fabrication process of a three-dimensional object.

While three-dimensional objects described herein have been described as being formed from a single resin, it should be appreciated that the devices, systems, and methods of the present disclosure have been described in this way sake of clarity and efficiency of explanation and, unless otherwise specified, any one or more of the devices, systems, and methods described herein can operate using more than one resin. Thus, more specifically, a plurality of resins can be combined on-demand to impart desired variations in aesthetic and/or physicochemical properties in a three-dimensional object being formed. That is, the plurality of resins can be combined to impart layer-by-layer variations along the three-dimensional object and, additionally or alternatively, can be combined to impart intralayer variations along the three-dimensional object. For example, in instances in which different colors are desirable in a finished part, resins with particles of different colors (e.g., red, green, and blue) can be combined on demand for a given layer or a given portion of a layer of the three-dimensional object for high-resolution control over the color of a finished part formed from the three-dimensional object. As an additional or alternative example, in instances in which different physicochemical properties are desirable in a finished part, a plurality of resins with different types of particles can be combined on-demand such that the aggregate combination of the plurality of resins includes a distribution of particles thermally processable to form the target variation in physicochemical properties along a finished part formed from the three-dimensional object.

In certain implementations, a resin can be provided on demand to facilitate formation of an interface layer between one or more support structures and the three-dimensional object being formed. The interface layer can inhibit bonding of one or more support structures to the three-dimensional object during thermal processing and/or debinding, thus facilitating removal of the one or more support structures during fabrication of a finished part. That is, support structures can be usefully incorporated into the three-dimensional object to reduce the likelihood of unintended sagging or other distortion associated with certain structural features. However, in instances in which such support structures are not intended to form a portion of the finished part, one or more resins can be selectively provided in all or a portion of a given layer to form the interface layer.

The one or more resins can include one or more components useful for inhibiting bonding of the one or more support structures to the three-dimensional object and, in general, the one or more components can inhibit bonding by imparting locally certain physicochemical properties to the interface layer. For example, material in the one or more of the resins forming the interface layer can be dissolvable for removal with a solvent prior to sintering the three-dimensional object. Additionally, or alternatively, material in the one or more resins forming the interface layer can have a shrinkage rate differing from a shrinkage rate of one or more resins forming the three-dimensional object away from the interface layer, with the difference in shrinkage rates facilitating separation of the interface layer from the three-dimensional object during sintering and/or debinding. As still a further or alternative example, the particles in the one or more resins forming the interface layer can include a ceramic material while one or more resins forming the three-dimensional object away from the interface layer can include metal. The ceramic material in the interface layer can shrink less than the metal in the three-dimensional object during thermal processing.

The above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the systems and methods described above may be embodied in any suitable transmission or propagation medium carrying computer-executable code and/or any inputs or outputs from same.

The method steps of the implementations described herein are intended to include any suitable method of causing such method steps to be performed, consistent with the patentability of the following claims, unless a different meaning is expressly provided or otherwise clear from the context. So, for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A method for the stereolithographic fabrication of a three-dimensional object as a plurality of successive layers, comprising the steps of:
provided a layer of resin, wherein the resin includes a first binder having a melt temperature, a second binder that is immiscible in the first binder and which cross-links or polymerizes upon sufficient exposure to light of a predetermined wavelength, and at least one of ceramic particles and metal particles, wherein the resin has a temperature above the melt temperature of the first binder;
exposing a portion of the layer of resin to a pattern of light from a light source to cure the portion of the layer of resin into one of the plurality of the successive layers by curing the second binder without curing the first binder;
repeating the steps of providing a layer of resin and exposing a portion of the layer of resin to a pattern of light to form a green form of the three-dimensional;
conducting a first debinding process to debind the first binder, wherein during the first debinding process the first binder is at a temperature above the melt temperature;
conducting a second debinding process to debind the second binder; and
thermally processing the green form of the three-dimensional object until the at least one of ceramic particles and metal particles densify to a finished form of the three-dimensional object.

2. The method of claim 1 wherein the first debinding process includes debinding the first binder by exposing the green form of the three-dimensional object to water.

3. The method of claim 1 wherein the first debinding process includes thermally debinding the first binder.

4. The method of claim 3 wherein the second debinding process includes thermally debinding the second binder.

5. The method of claim 4 wherein the light source is a digital light processing (DLP) projector controllable to project an image on the resin.

6. The method of claim 5 wherein the step of thermally processing of the green form of the three-dimensional object includes sintering the at least one of ceramic particles and metal particles.

7. The method of claim 6 wherein the step of thermally processing the green form of the three-dimensional object includes infiltrating the green form of the three-dimensional object.

8. The method of claim 7 wherein during the step of providing a layer of resin a film is moved in an indexed fashion in a direction having a component parallel to the layer of resin.

9. The method of claim 1, wherein the first binder is a wax.

10. The method of claim 1, wherein the first binder is at least one selected from the group consisting of paraffin wax, carnauba wax, stearic acid, polyethylene glycol, polyoxymethylene, oleic acid, and dibutyl phthalate.

11. The method of claim 1, wherein the second binder is at least one selected from the group consisting of poly (methyl methacrylate), polyethylene glycol diacrylate, urethane oligomers functionalized to acrylate groups, epoxy oligomers functionalized to acrylate groups, 1,6-Hexanediol acrylates, and styrene.

* * * * *

UNITED STATES PATENT AND TRADEMARK OFFICE
CERTIFICATE OF CORRECTION

| | |
|---|---|
| PATENT NO. | : 11,826,949 B2 |
| APPLICATION NO. | : 16/328448 |
| DATED | : November 28, 2023 |
| INVENTOR(S) | : Michael Andrew Gibson et al. |

It is certified that error appears in the above-identified patent and that said Letters Patent is hereby corrected as shown below:

On the Title Page

Item (63), before "application No. 62/474,014" delete "Continuation-in-part of" and insert --Provisional--

Item (63), before "application No. 62/421,716" delete "and a continuation-in-part of" and insert --provisional--

Signed and Sealed this
Ninth Day of January, 2024

Katherine Kelly Vidal
*Director of the United States Patent and Trademark Office*